(12) United States Patent
Raniere

(10) Patent No.: US 9,687,388 B2
(45) Date of Patent: Jun. 27, 2017

(54) METHOD, SYSTEM, AND APPARATUS FOR PROTECTING MAMMALIAN TISSUE REGIONS

(71) Applicant: Joseph Raniere, Peachtree City, GA (US)

(72) Inventor: Joseph Raniere, Peachtree City, GA (US)

(*) Notice: Subject to any disclaimer, the term of this patent is extended or adjusted under 35 U.S.C. 154(b) by 409 days.

(21) Appl. No.: 14/093,059

(22) Filed: Nov. 29, 2013

(65) Prior Publication Data

US 2014/0305446 A1    Oct. 16, 2014

Related U.S. Application Data

(60) Provisional application No. 61/812,054, filed on Apr. 15, 2013.

(51) Int. Cl.
*A61F 13/14* (2006.01)
*A61F 13/00* (2006.01)

(52) U.S. Cl.
CPC ............ *A61F 13/14* (2013.01); *A61F 13/141* (2013.01); *A61F 2013/00272* (2013.01)

(58) Field of Classification Search
CPC .......... A61F 15/008; A61F 2013/00165; A61F 2013/00272; A61F 2013/0057; A61F 13/14; A61F 13/141; A61F 13/145
See application file for complete search history.

(56) References Cited

U.S. PATENT DOCUMENTS

| | | | |
|---|---|---|---|
| 697,637 A * | 4/1902 | Lee ...................... | A61F 15/008 128/888 |
| 3,063,555 A | 11/1962 | Hanington | |
| 4,054,140 A | 10/1977 | Etes | |
| 4,754,750 A | 7/1988 | Imonti | |
| 4,870,977 A | 10/1989 | Imonti | |
| 5,026,394 A | 6/1991 | Baker | |
| 5,032,103 A | 7/1991 | Larsson | |
| 5,425,762 A | 6/1995 | Muller | |
| 5,855,606 A | 1/1999 | Eaton | |
| 6,274,787 B1 * | 8/2001 | Downing .............. | A61F 15/008 602/14 |
| 6,468,295 B2 | 10/2002 | Augustine | |
| D493,000 S | 7/2004 | Grady | |
| 7,265,256 B2 * | 9/2007 | Artenstein ............ | A61F 15/008 128/888 |
| 7,487,779 B2 | 2/2009 | Kurz | |
| 7,921,851 B2 | 4/2011 | Kurz | |
| 7,938,122 B2 | 5/2011 | Clark | |

(Continued)

FOREIGN PATENT DOCUMENTS

AU    B-66138/94    1/1996
WO    WO 02/068038    9/2002

(Continued)

OTHER PUBLICATIONS

Scott L. Spear, The Nipple Guard: An Alternative Covering for Nipple-Areola Reconstructions with or without Skin Grafts, Plastic and Reconstructive Surgery, Nov. 1997, 1509-1512.

*Primary Examiner* — Kari Rodriquez
(74) *Attorney, Agent, or Firm* — Merle W. Richman, III

(57) ABSTRACT

Embodiments of a system and method for protecting mammalian tissue regions, the system including a removable guard cap. Other embodiments may be described and claimed.

13 Claims, 28 Drawing Sheets

(56) References Cited

U.S. PATENT DOCUMENTS

| | | |
|---|---|---|
| 8,191,554 B2 | 6/2012 | Kurz |
| 2002/0029010 A1 | 3/2002 | Augustine |
| 2007/0087042 A1* | 4/2007 | Thomas ................ A61F 13/063 424/445 |
| 2012/0277648 A1 | 11/2012 | Kendall |
| 2014/0060548 A1* | 3/2014 | Check .................. A61F 15/008 128/845 |

FOREIGN PATENT DOCUMENTS

| | | |
|---|---|---|
| WO | WO 03/032828 | 4/2003 |
| WO | WO 03/073978 | 9/2003 |
| WO | WO 2012/060546 | 5/2012 |

\* cited by examiner

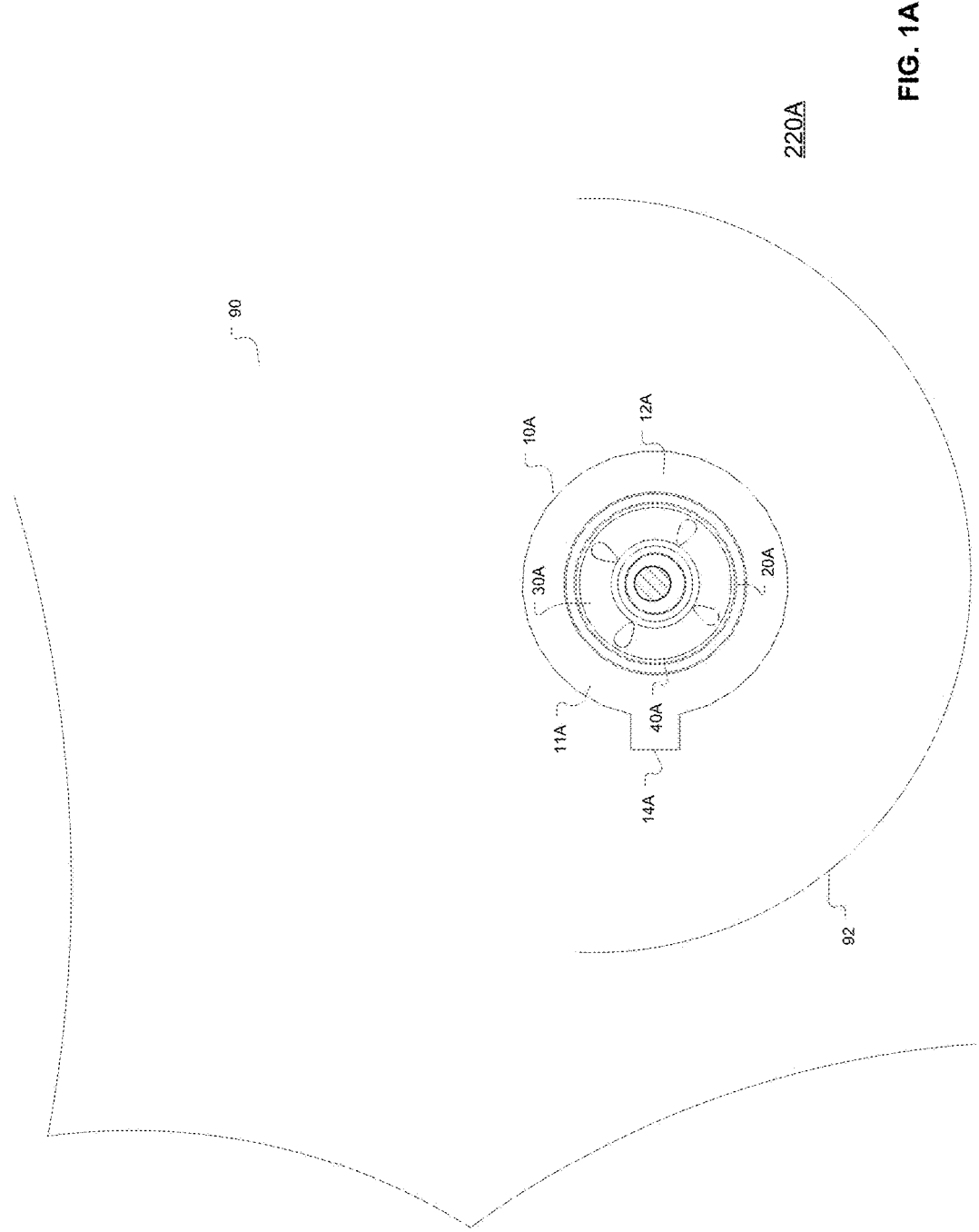

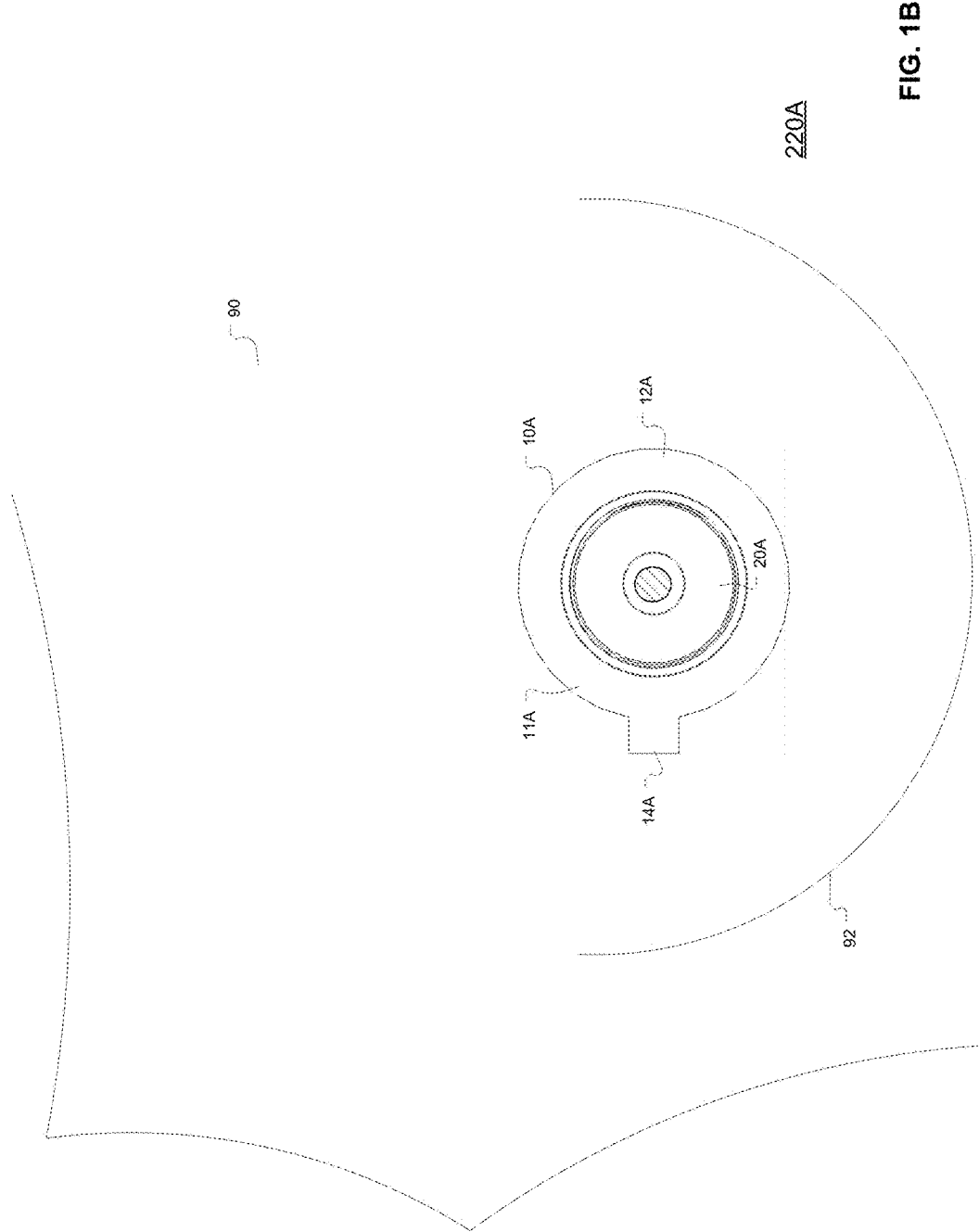

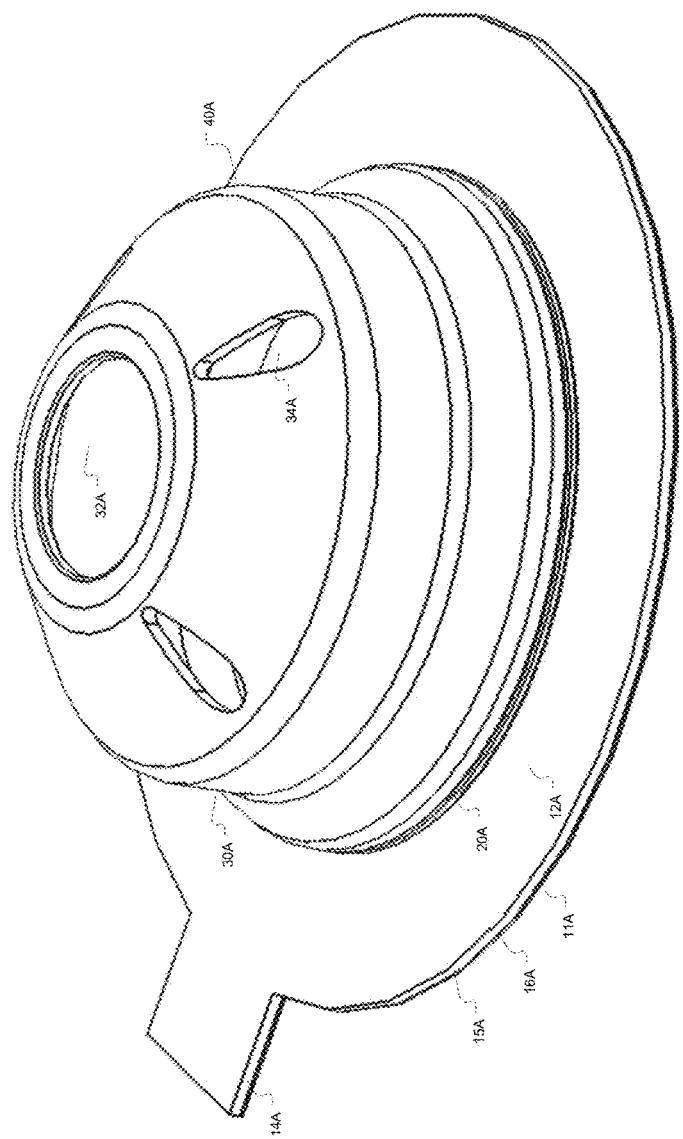

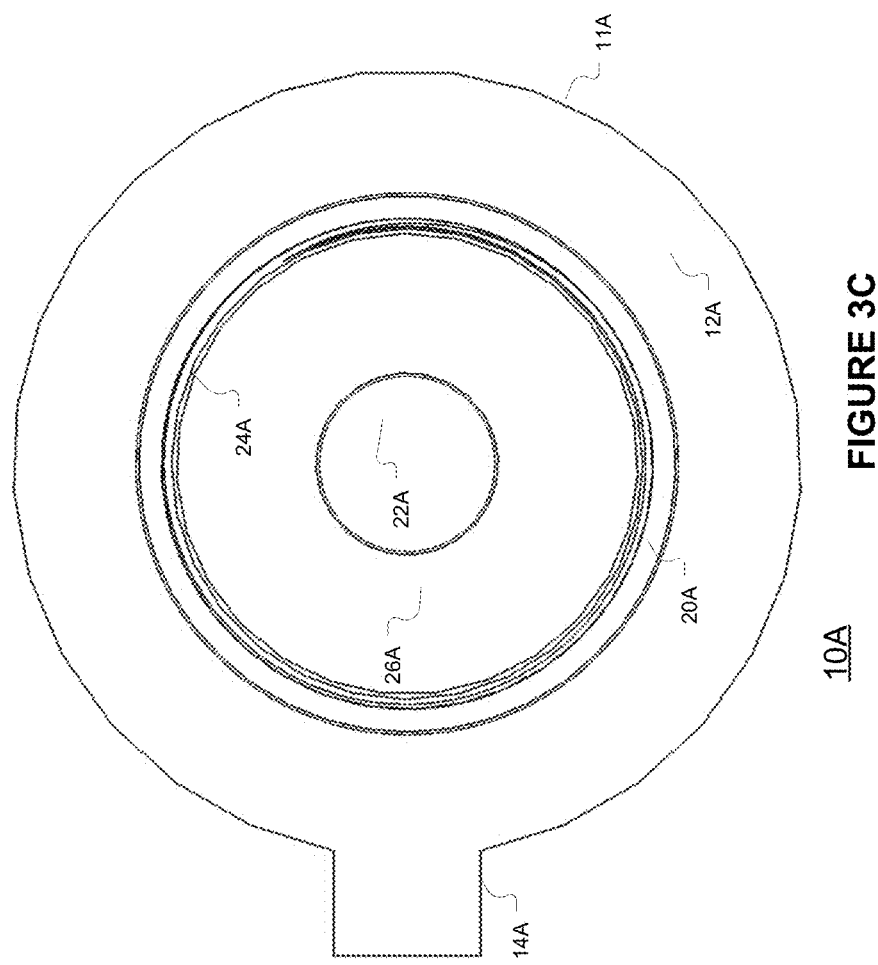

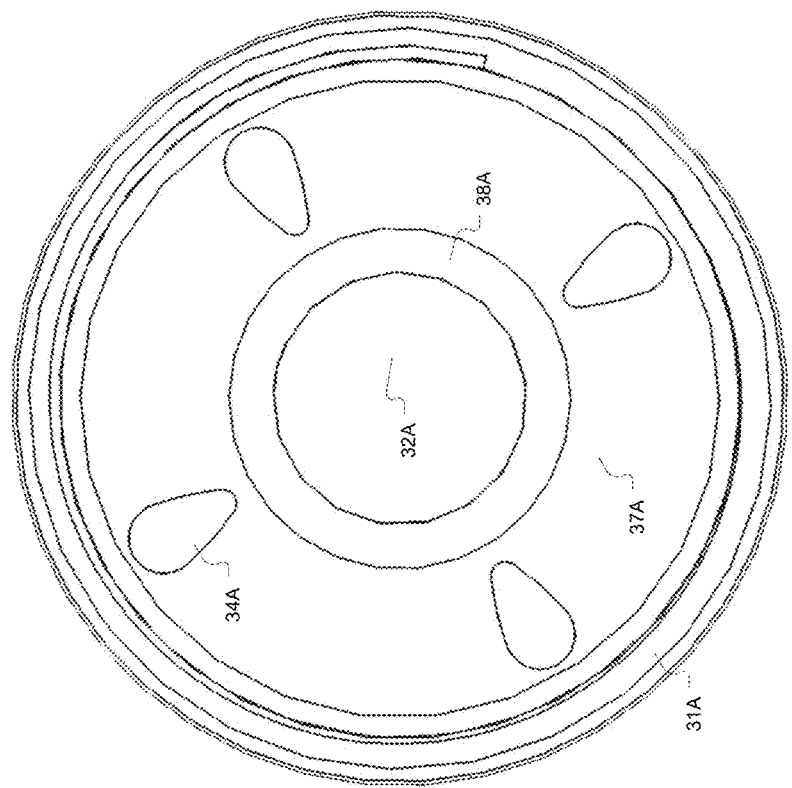
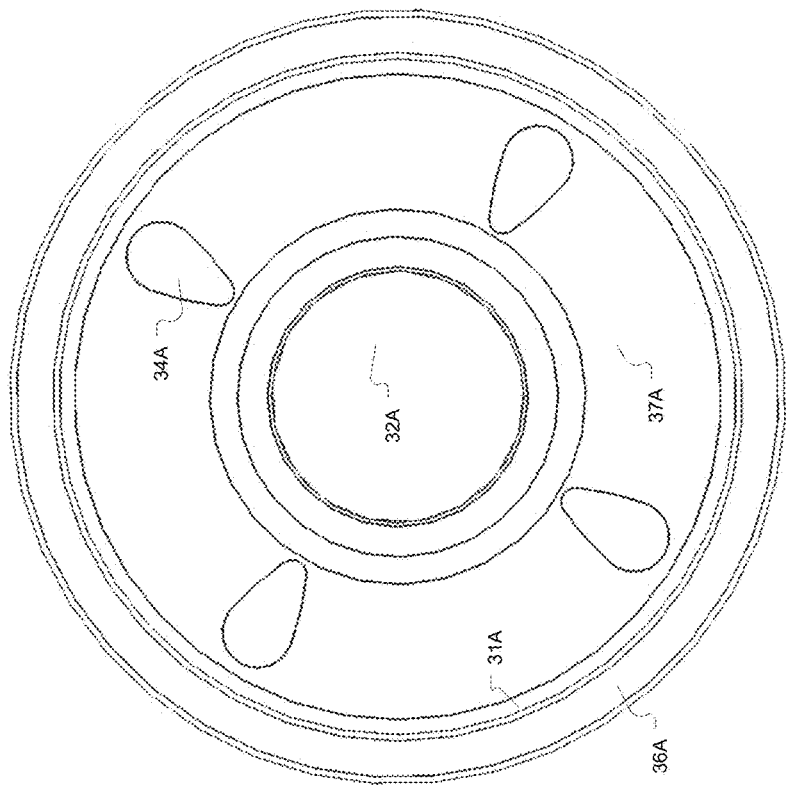

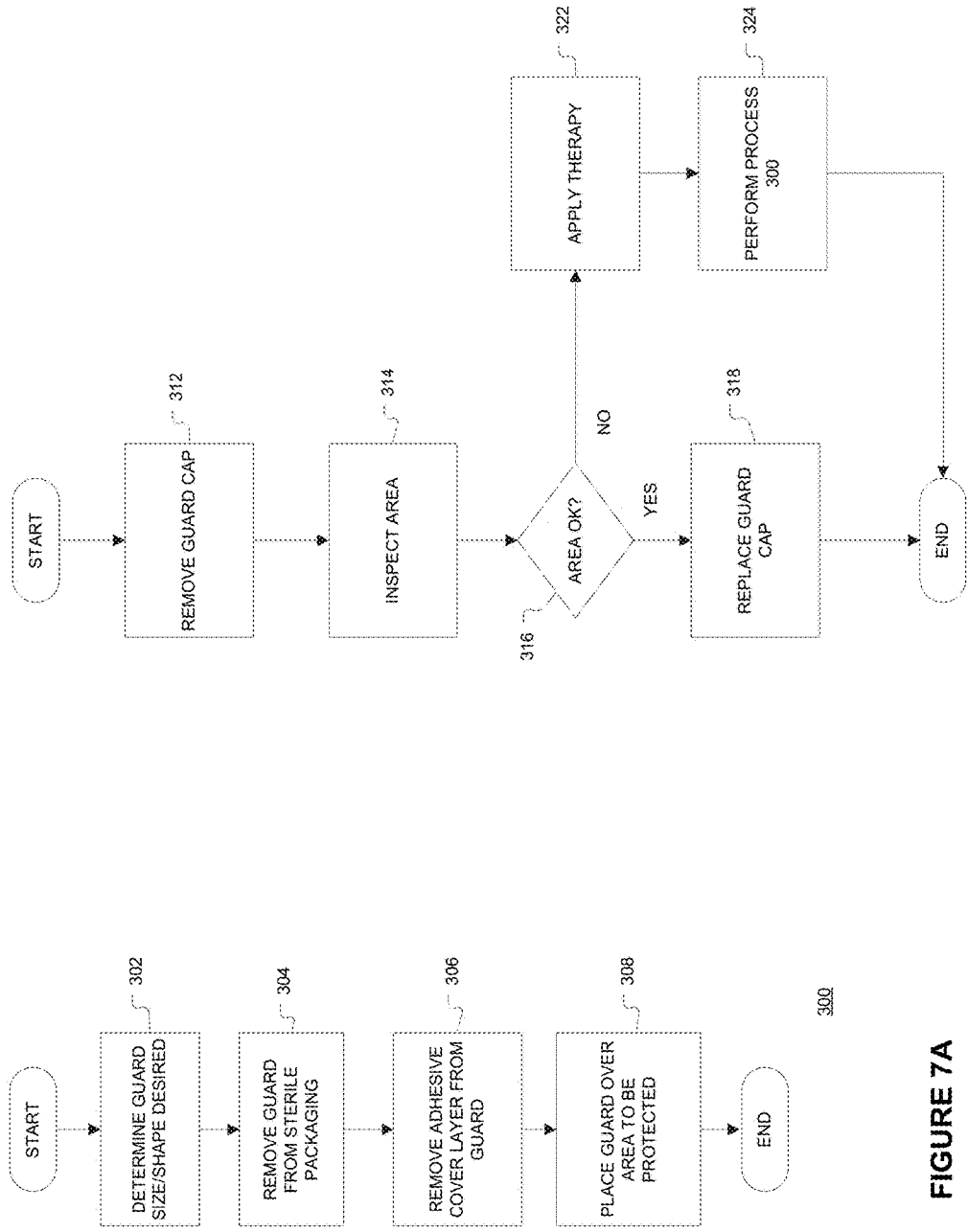

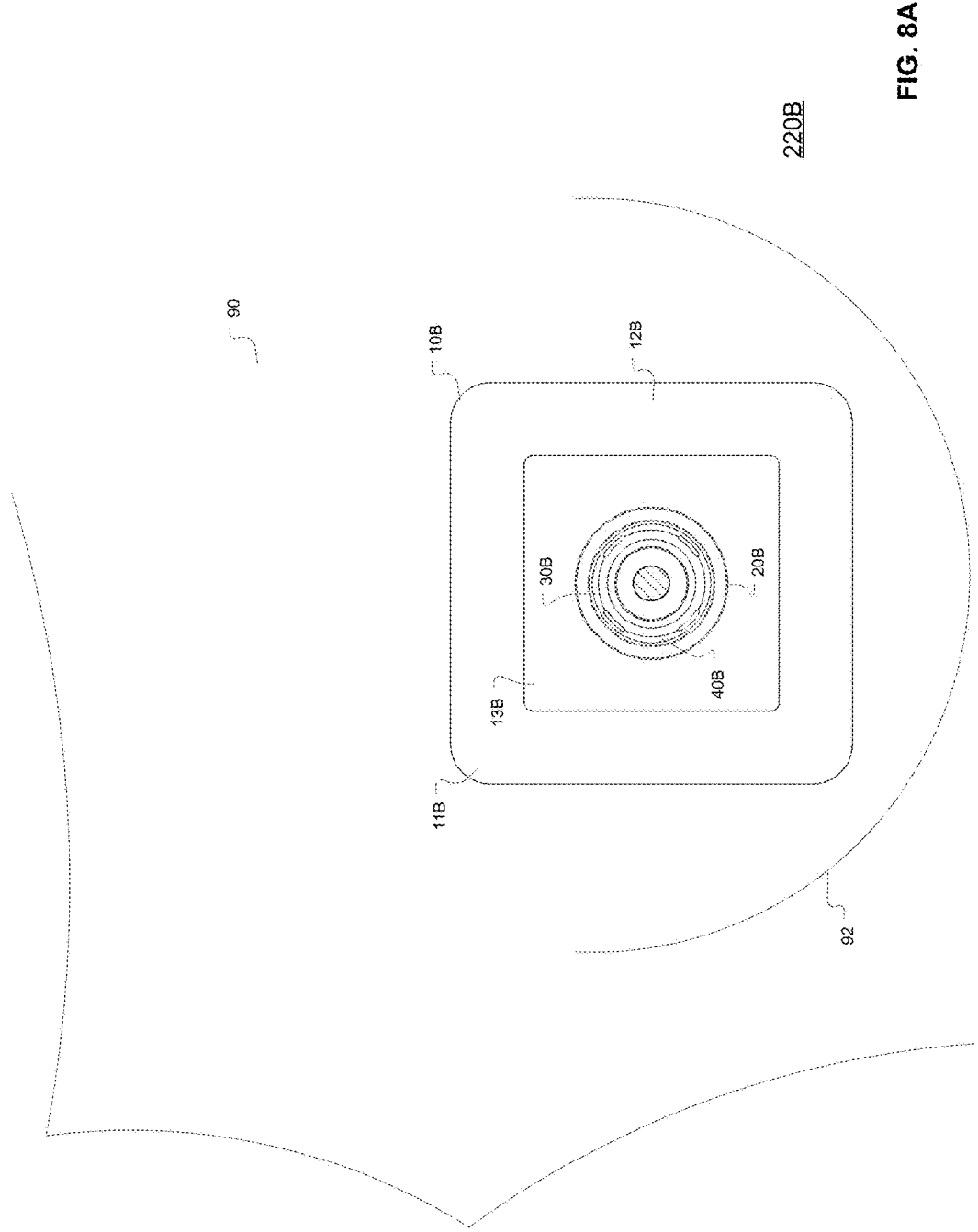

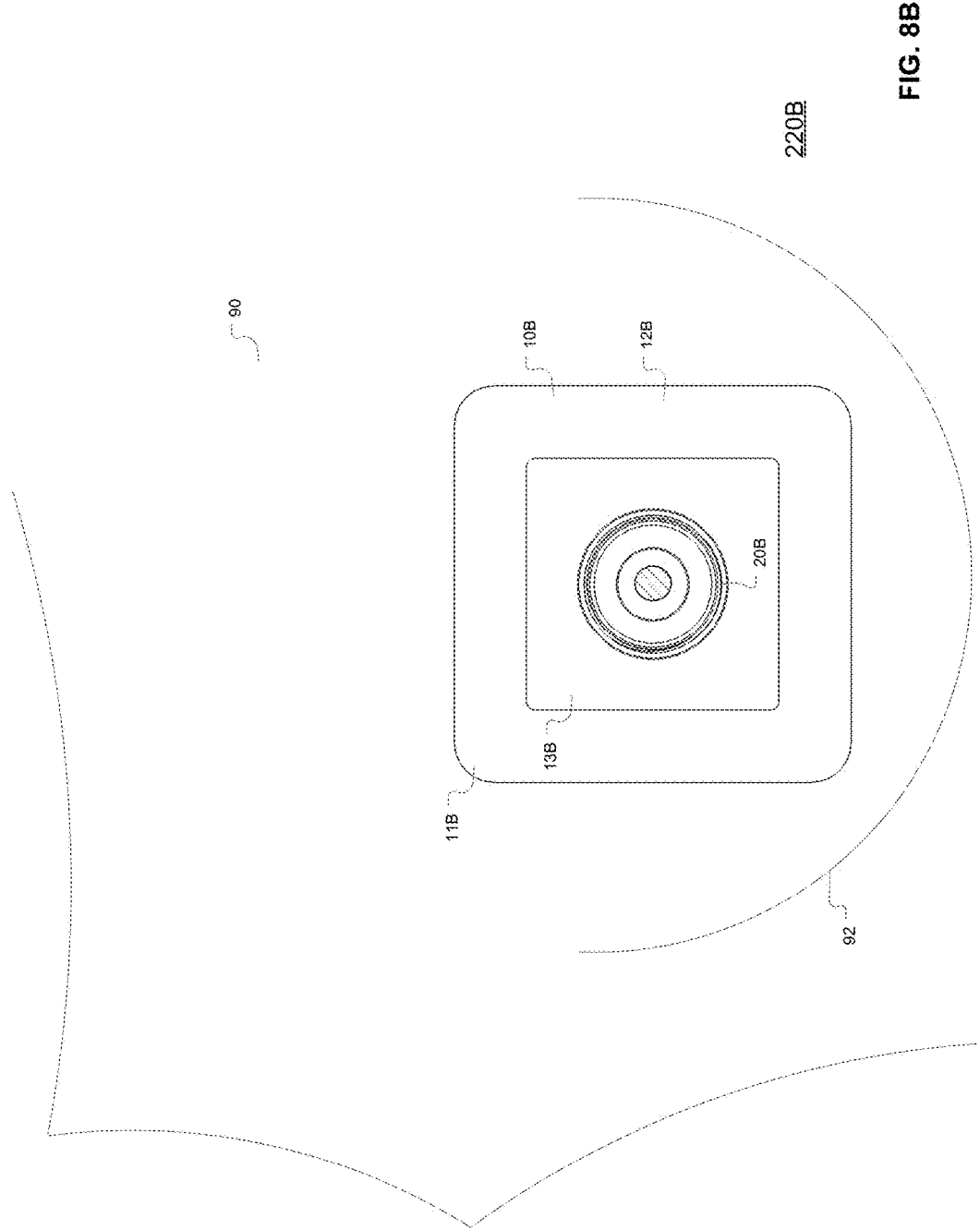

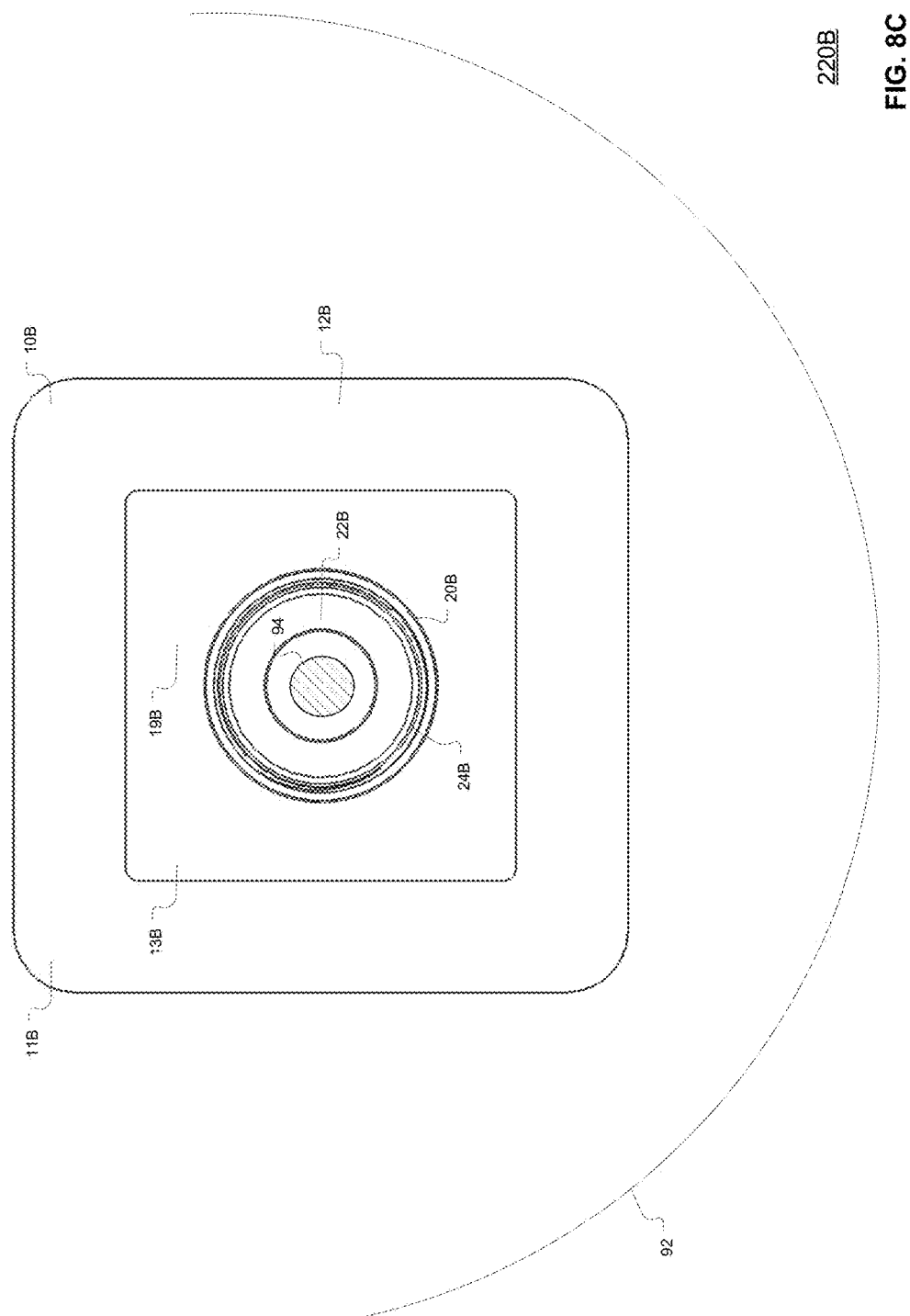

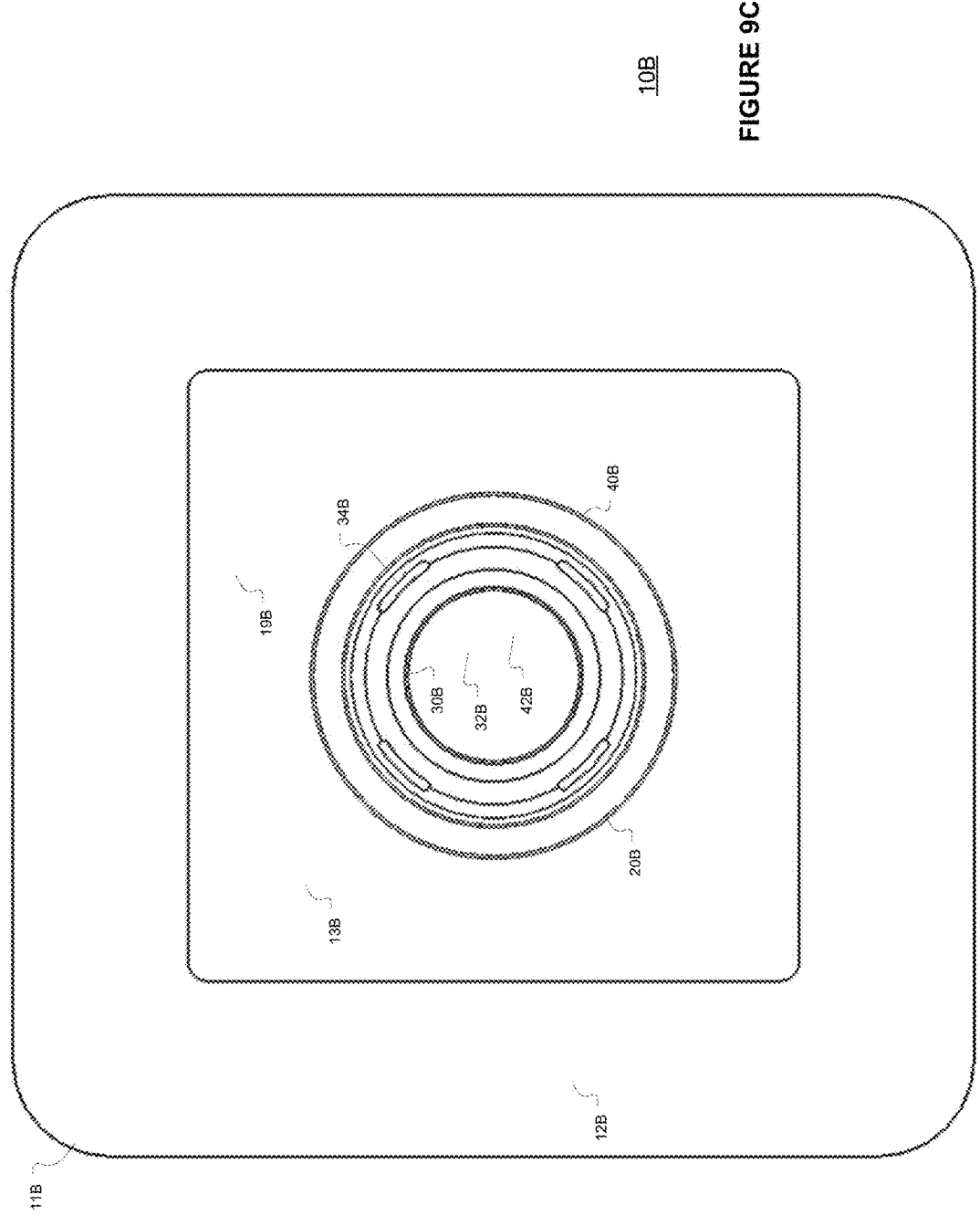

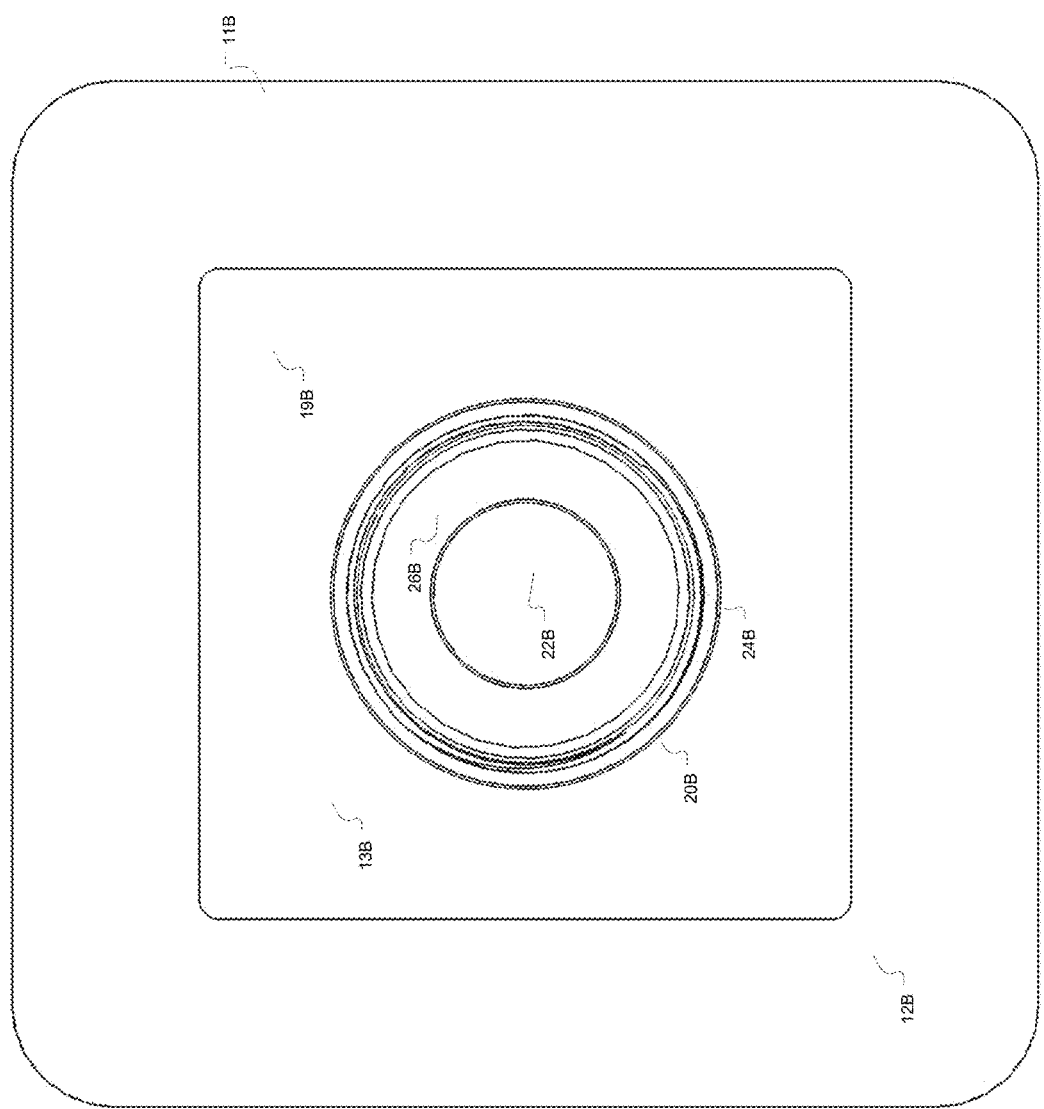

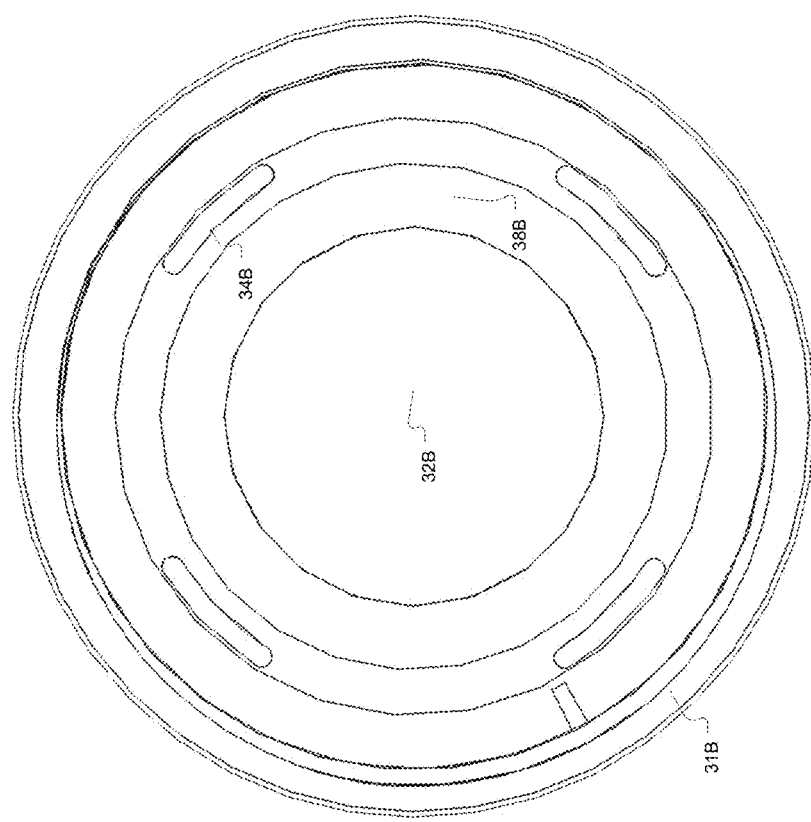
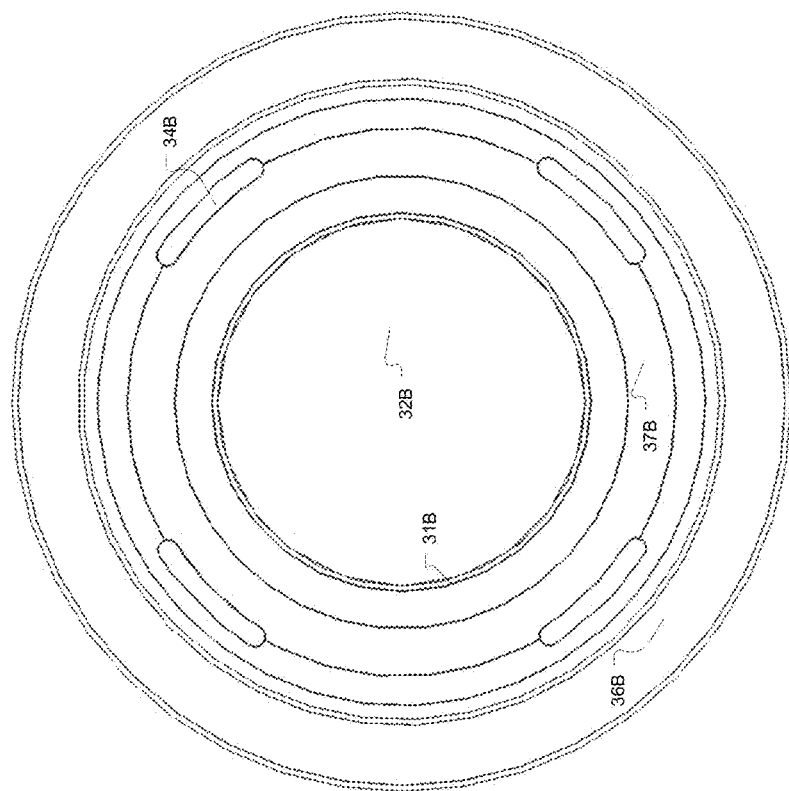

_METHOD, SYSTEM, AND APPARATUS FOR PROTECTING MAMMALIAN TISSUE REGIONS_

CROSS REFERENCE TO RELATED APPLICATIONS

The present application is related to U.S. Provisional Application 61/812,054, filed Apr. 15, 2013, and entitled "METHOD, SYSTEM, AND APPARATUS FOR PROTECTING MAMMALIAN TISSUE REGIONS", which is incorporated by reference in its entirety.

TECHNICAL FIELD

Various embodiments described herein relate generally to protecting mammalian tissue regions, including systems and methods for protecting a mammalian tissue region.

BACKGROUND INFORMATION

It may be desirable to protect a mammalian tissue region, in particular a skin region.

BRIEF DESCRIPTION OF THE DRAWINGS

FIG. 1A is a simplified diagram of mammalian tissue region protection architecture according to various embodiments.

FIG. 1B is a simplified diagram of mammalian tissue region protection architecture with guard cap removed according to various embodiments.

FIG. 2A is a simplified, isometric side view of a mammalian tissue region protection system according to various embodiments.

FIG. 3C is a simplified, top view of a mammalian tissue region protection system without the guard cap according to various embodiments.

FIG. 4C is a simplified, top view of a mammalian tissue region protection system guard cap according to various embodiments.

FIG. 4D is a simplified, bottom view of a mammalian tissue region protection system guard cap according to various embodiments.

FIG. 7A-7B are flow diagrams illustrating mammalian tissue region protection processing algorithms according to various embodiments.

FIG. 8A is a simplified diagram of another mammalian tissue region protection architecture according to various embodiments.

FIG. 8B is a simplified diagram of another mammalian tissue region protection architecture with guard cap removed according to various embodiments.

FIG. 8C is a simplified diagram of another mammalian tissue region protection architecture with guard cap removed according to various embodiments.

FIG. 9C is a simplified, top view of another mammalian tissue region protection system according to various embodiments.

FIG. 10C is a simplified, top view of another mammalian tissue region protection system without the guard cap according to various embodiments.

FIG. 11C is a simplified, top view of another mammalian tissue region protection system guard cap according to various embodiments.

FIG. 11D is a simplified, bottom view of another mammalian tissue region protection system guard cap according to various embodiments.

DETAILED DESCRIPTION

FIGS. 1A and 8A are simplified diagrams of mammalian tissue region protection (MTRP) architecture 220A, 220B according to various embodiments. Architecture 220A, 220B includes MTRP systems 10A, 10B coupled to a mammalian tissue region 92 of a mammalian upper torso section 90. In an embodiment, a MTRP system 10A, 10B may include a skin and guard coupling module 11A, 11B and a raised guard module 40A, 40B. A raised guard module 40A, 40B may include a base module 20A, 20B and a cap module 30A, 30B.

A cap module 30A, 30B may be releasably coupled to the base module 20A, 20B via interlocks or threads in an embodiment. The cap module 30A, 30B may extend vertically from the base module 20A, 20B to provide a raised, open area. A cap module 30A, 30B and base module 20A may be rigid or semi-rigid and be formed from medical grade polymers, silicon, ceramics, metal, alloys, or combinations thereof. In an embodiment, the cap module 30A, 30B and base module 20A, 20B may be radiographically opaque.

In an embodiment, the guard module 40A, 40B base module 20A, 20B may be securely coupled to the skin and guard coupling module 11A, 11B. A base module 20A, 20B may be coupled to skin and guard coupling module 11A, 11B non-absorbent cover section 19A, 19B via an adhesive or ultrasonic weld. The skin and guard coupling module 11A, 11B may include an adhesive skin coupling module 12A, 12B and a non-adhesive module 13A, 13B.

Figure 9A:
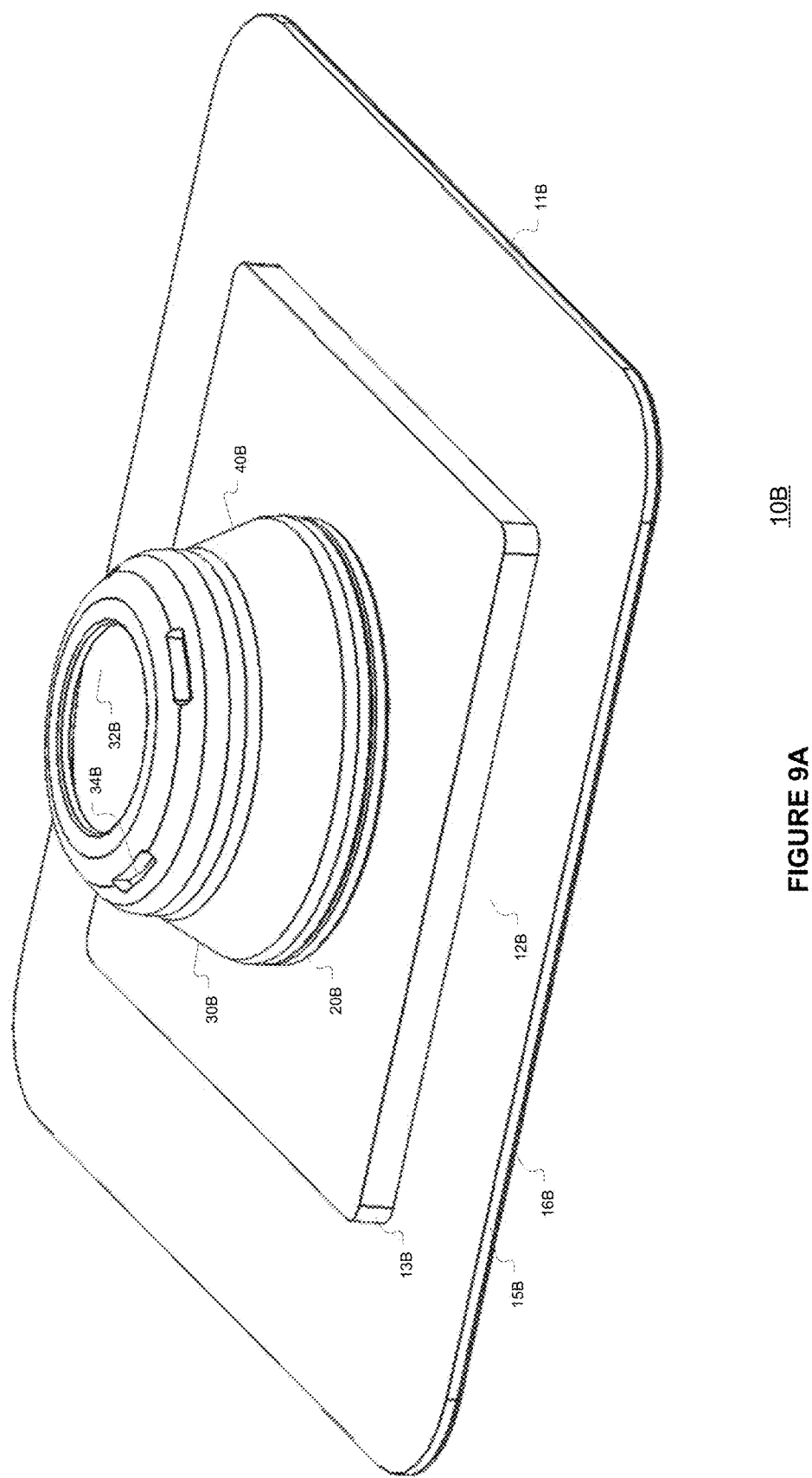
FIG. 9A is a simplified, isometric side view of another mammalian tissue region protection system according to various embodiments.

In an embodiment, an adhesive skin coupling module 12A, 12B may include an adhesive layer 15A, 15B initially covered with a non-stick layer or film 16A, 16B (FIGS. 2A, 9A). An adhesive skin coupling module 12A, 12B may include a tab section 14A. In an embodiment, the tab section 14A may not include an adhesive layer section 15A, 15B to provide a grip section to enable a user or physician to de-couple the skin and guard coupling module 11A, 11B from a tissue region 92 as desired.

The non-adhesive module 13A, 13B may be coupled to the adhesive module 12A about its periphery in an embodiment. The non-adhesive module 13A, 13B may include an absorbent section 18A, 18B (FIGS. 2D, 9D), a non-absorbent cover section 19A, 19B (FIGS. 1C, 8C), and a fenestration 17A, 17B (FIGS. 2D, 9D) through the non-absorbent cover section 19A, 19B and absorbent section 18A, 18B. The absorbent section 18A, 18B may including several layers to enable the absorption of exudate and reduce risk of maceration. The absorbent section 18A, 18B may be formed of medically approved absorbent material including cotton, other natural fibers, and man-made fibers. The cover section 19A, 19B and adhesive section 12A, 12B cover may be formed of a moisture vapor permeable material including silicone in an embodiment.

Figure 1C:
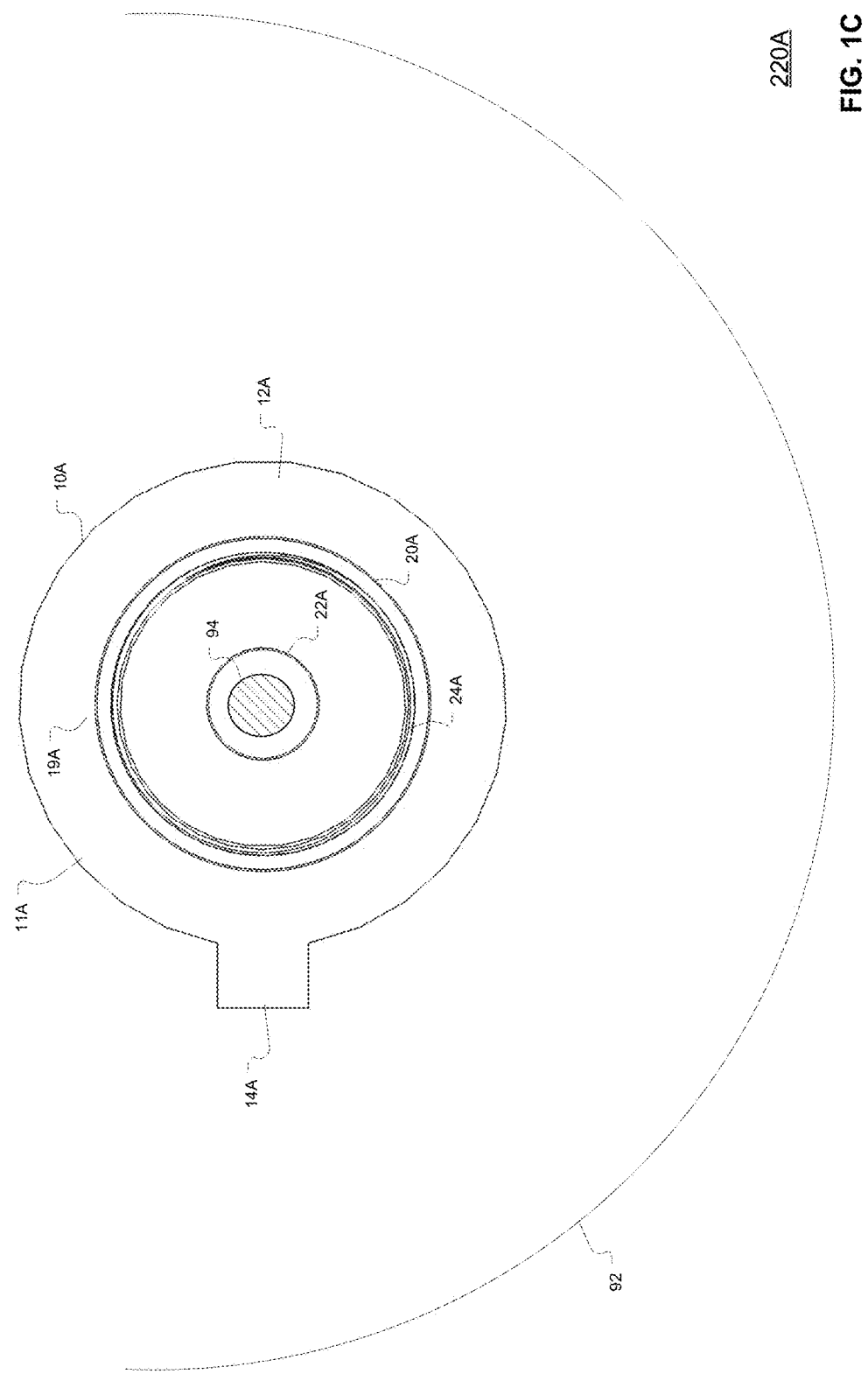
FIG. 1C is a simplified diagram of mammalian tissue region protection architecture with guard cap removed according to various embodiments.

In an embodiment, the fenestration 17A, 17B may be central to the skin and guard coupling module 11A, 11B. The fenestration 17A, 17B may also be circular, elliptical, square, or have another shaped opening. As shown in FIGS. 1C and 8C, a sensitive skin region 94 to be protected may be centered or located over the fenestration 17A, 17B to enable the skin region 94 to be aerated. A guard module 40A, 40B may also include a fenestration 42A, 42B (FIGS. 2A, 9A) formed by a base module 20A, 20B fenestration 22A, 22B (FIGS. 1C, 8C) and the cap module 30A, 30B fenestration 32A, 32B (FIGS. 2A, 9A).

In an embodiment, the guard modules 40A, 40B fenestrations 32A, 32B may be axial with the skin and guard coupling module 11A, 11B fenestrations 17A, 17B to enable visualization of the skin region 94 and maximize aeration of the skin region 94. It is noted that the skin region 94 may protrude above or higher than the neighboring skin region 92. The guard module 40A, 40B cap module 30A, 30B axial height or dimensions may be selected to ensure a cap module 30A, 30B does not touch the skin region 94.

In an embodiment, the adhesive layer 15A, 15B may include a Tegaderm, 3M Medpore, or other dermal tape adhesive. An adhesive layer 15A, 15B may also include Avery Dennison products 1827A, 1827S, 5576A, ConvaTec products Duoderm Ultrathin and Signal Duoderm, and Hollister product Adapt Barrier Ring. An adhesive layer 15A, 15B may further include an antimicrobial agent including silver. In an embodiment, the skin and guard coupling module 11A, 11B may include a bandage that has been modified to include a central fenestration 17A, 17B. In an embodiment the bandage may be a Mepilex Border with Safetac Technology dressing manufactured by Molnlycke Health Care.

As shown in FIGS. 1A to 1C and 8A to 8C, a MTRP system 10A, 10B may be employed to protect a dermal or skin region 92. A MTRP system 10A, 10B and accordingly, the skin and guard coupling module 11A, 11B and guard module 40A, 40B size and shape may be selected or configured according to the dermal or tissue region to be protected. In an embodiment, the tissue region 92 to be protected may be a breast region 92 including a nipple or nipple construct (sensitive tissue region) 94 (shown in FIGS. 1C, 8C). During breast surgeries including enhancements, reconstructions and mastectomies, a nipple 94 may be moved or a construct representing a nipple may be formed from raised, local skin flaps or myocutaneous flaps. The resultant nipple or construct 94 may be extremely sensitive and include suture lines about the nipple or construct 94. Further, it may be desirable to provide a MTRP system 10A, 10B that has a raised or offset section (guard cap module 30A, 30B) (from the skin 92, nipple or construct 94) to prevent nipple or construct 94 compression or flattening.

FIGS. 1B, 1C, 8B, and 8C are simplified diagrams of MTRP architecture 220A, 220B with the MTRP system 10A, 10B, guard module 40A, 40B cap module 30A, 30B removed according to various embodiments. As shown in FIGS. 1B, 1C, 8B, and 8C, a MTRP system 10A, 10B guard module 40A, 40B base module 20A, 20B may include external threads 24A, 24B (FIGS. 3A-C, 10A-C) configured to mateably couple with internal threads 31A, 31B (FIGS. 4D, 11C) of a cap module 30A, 30B. The thread combination 24A, 31A and 24B, 31B may enable a guard module 40A, 40B cap module 30A, 30B to be rotatably and securely installed on its base module 20A, 20B to protect a tissue or skin region 92, 94 including a raised tissue region 94. The thread combination 24A, 31A and 24B, 31B may also enable the guard module's 40A, 40B cap module 30A, 30B to be rotatably removed from its base module 20A, 20B to expose, treat, or inspect a region 92, 94. In an embodiment the guard module 40A, 40B base module 20A, 20B and cap module 30A, 30B may be formed of a hypoallergenic material including elastomers, silicon, metal, metal alloys, combinations thereof, or other medical grade materials.

In an embodiment, the MTRP system 10A, 10B may be sized to protect a nipple or nipple construct 94. In such an embodiment, a MTRP system 10A guard module 40A may have a diameter from about 3.5 cm to 7 cm, the skin and guard coupling module 11A non-adhesive section 13A (FIG. 2C) may have a length of about 3 to 9 cm and a width of about 0.5 cm to 3 cm. In an embodiment a guard module 40A may be circular in shape. The guard module 40A overall height may be about 1.0 cm to 3.0 cm (open area about skin region 92). The guard module 40A central fenestration 42A (formed by the cap module 30A fenestration 32 (FIG. 2A) and the base module 20 fenestration 22A (FIG. 1C) may have a diameter of about 1.0 cm to 3.0 cm. The skin and guard coupling module 11A fenestration 17A may be aligned with the guard module 40A central fenestration 40A and have a diameter of about 1.0 cm to 3.0 cm.

The guard module 40B cap module 30B and corresponding base module 20B may have a diameter of about 2 to 5 cm and about 3.8 cm in an embodiment. The cap module 30B central fenestration 32B and the base module 20B fenestration 22B may have a diameter of about 1 to 3 cm and about 1.8 cm in an embodiment. The second section 37B of the cap module 30B may have a diameter of about 2 to 4 cm and about 3.1 cm in an embodiment. The cap module 30B offset fenestrations 34B may be about 0.3 to 0.8 cm length and about 0.63 cm, have a width of about 0.05 to 2.0 cm and about 0.12 cm, and formed about a circle having a diameter about 2.0 to 4.0 cm and about 2.8 cm in an embodiment. The base module 20B interlock 24B may have a diameter of about 2.0 to 4.5 cm and about 3.3 cm and a height of about 0.2 to 1.0 cm and about 0.45 cm in an embodiment.

The guard module 40B cap module 30B may have a height of about 1.0 cm to 3 cm and about 1.65 cm and the offset fenestrations 34B may be located about 0.8 to 2.8 cm a and about 1.4 cm from the cap module 30B bottom in an embodiment. As noted, a guard module 40A, 40B base module 20A, 20B fenestration 22A, 22B and a skin and guard coupling module 11A, 11B fenestration 17A, 17B may be sized and configured to provide an open region for a skin region 94 (nipple or construct in an embodiment). The fenestrations 22A, 22B, 17A, 17B openings may prevent construct 94 compression when placed over same. The fenestrations 22A, 22B, 17A, 17B along with the cap modules 30A, 30B fenestration 32A, 32B may also provide light and air to the region 92, 94 to stimulate a healing response and limit infections. In an embodiment, the skin and guard coupling module 11A may be circular, other than a tab 14A offset, and have an inner diameter of about 4 to 6 cm and an outer diameter of about 5 to 9 cm.

In an embodiment, a skin and guard coupling module 11B may be approximately square and have a side length of about 6 to 14 cm and about 10 cm in an embodiment. In an embodiment, a skin and guard coupling module 11B non-adhesive section 13B may be approximately square and have a side length of about 3 to 8 cm and about 6.3 cm and a height of about 0.1 to 0.5 cm and about 0.32 cm in in an embodiment. The skin and guard coupling module 11B adhesive section 12B may have a width of about 1 to 3 cm and about 1.8 cm in an embodiment. In an embodiment, a guard module 40A outer diameter may be about 4 to 6 cm and 5.5 cm in an embodiment and its height may be about 1 to 3 cm and 2.0 cm in an embodiment.

The guard module 40A base module fenestration 22, cap module 32, and skin and guard coupling module fenestration 17A may have a diameter of about 1 to 3 cm and about 1.8 cm in an embodiment. The skin and guard coupling module 11A non-adhesive section 13A may have a width about 1 to 2 cm and about 1.25 cm in an embodiment.

Figure 2B:
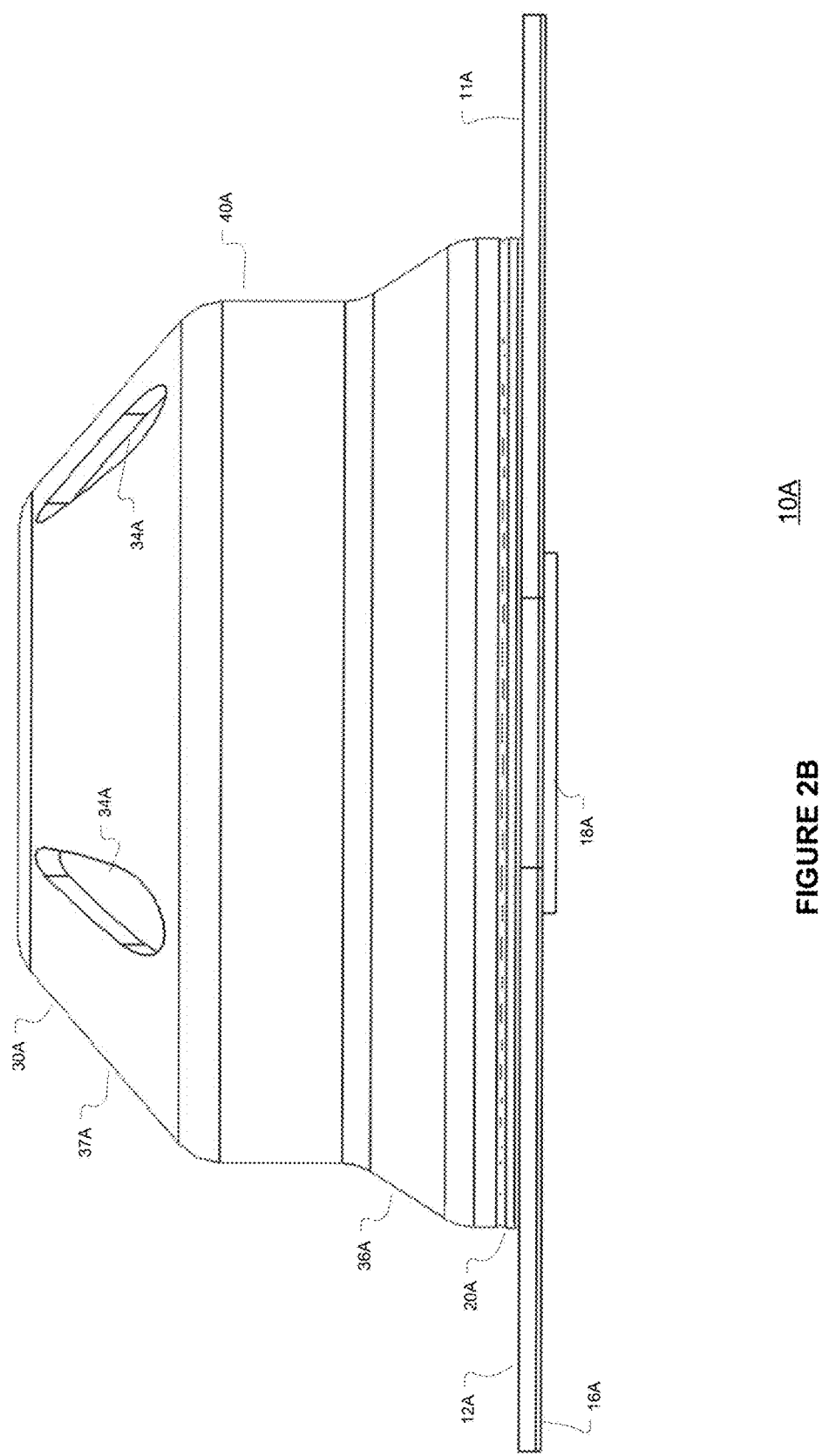
FIG. 2B is a simplified, side view of a mammalian tissue region protection system according to various embodiments.
Figure 9B:
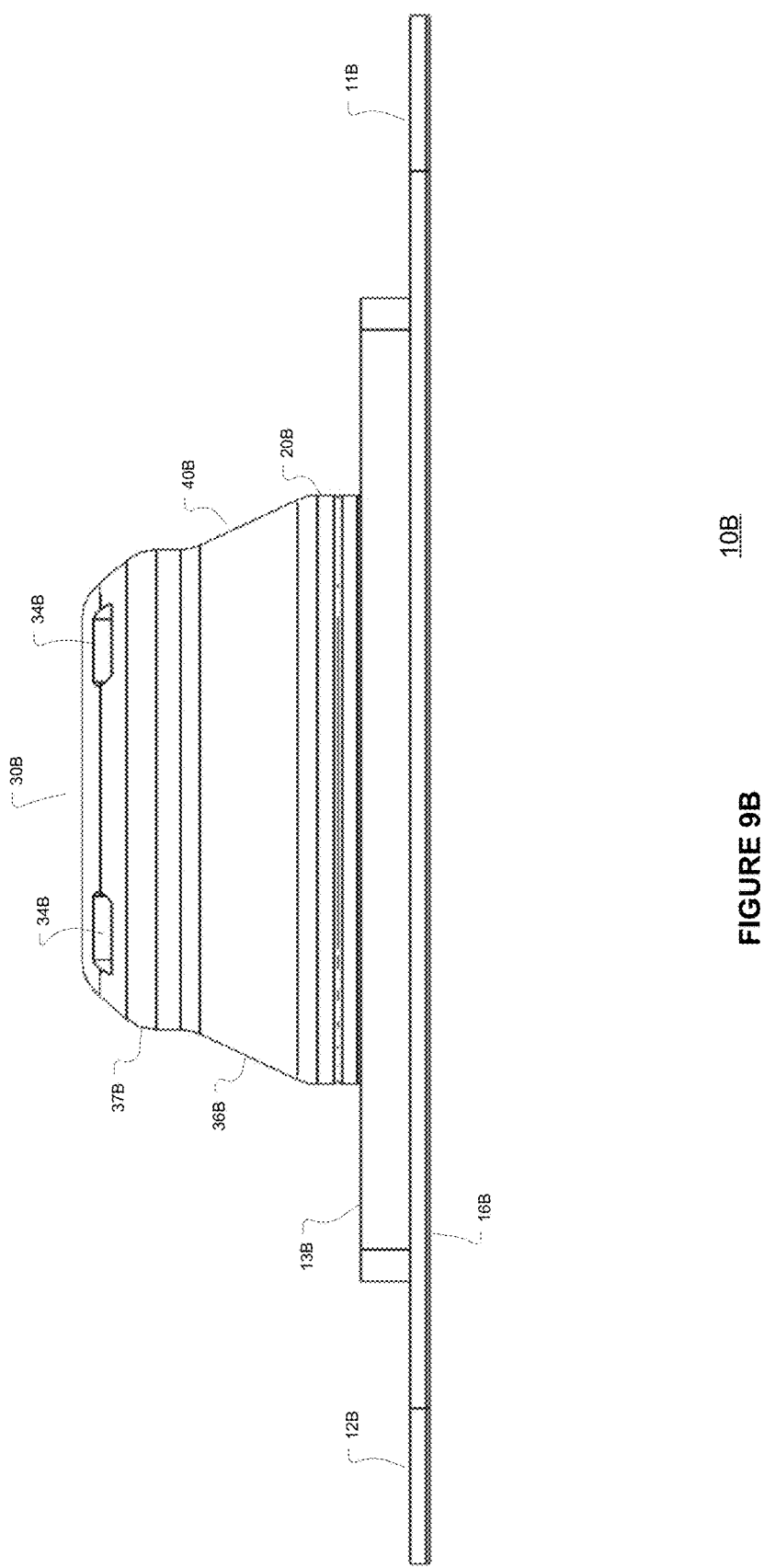
FIG. 9B is a simplified, side view of another mammalian tissue region protection system according to various embodiments.

FIGS. 2A and 9A are simplified isometric diagrams of MTRP systems 10A, 10B according to various embodiments. As shown in FIGS. 2A, 9A a guard module 40A, 40B cap module 30A, 30B may include a plurality of side fenestrations 34A, 34B (3 to 8 and 4 in an embodiment) in addition to its central fenestration 32A, 32B. A vertically offset, fenestrated, removable guard ring 30A, 30B (along with the skin and guard coupling module 11A, 11B fenestration 17A) may enable the communication of light and air to the region 92, 94 while protecting the area from impact or compression. FIGS. 2B, 9B are simplified side diagrams of MTRP systems 10A, 10B according to various embodiments. As shown in FIGS. 2B 2D, 9B, and 9D, a MTRP system 10A, 10B skin and guard coupling module may include a non-adhesive section 13A, 13B. The non-adhesive section 13A, 13B may be configured and sized to cover or protect one or more sutures or stitches adjacent a construct or surgery site 94 in addition to the construct or surgery site 94.

Figure 2D:
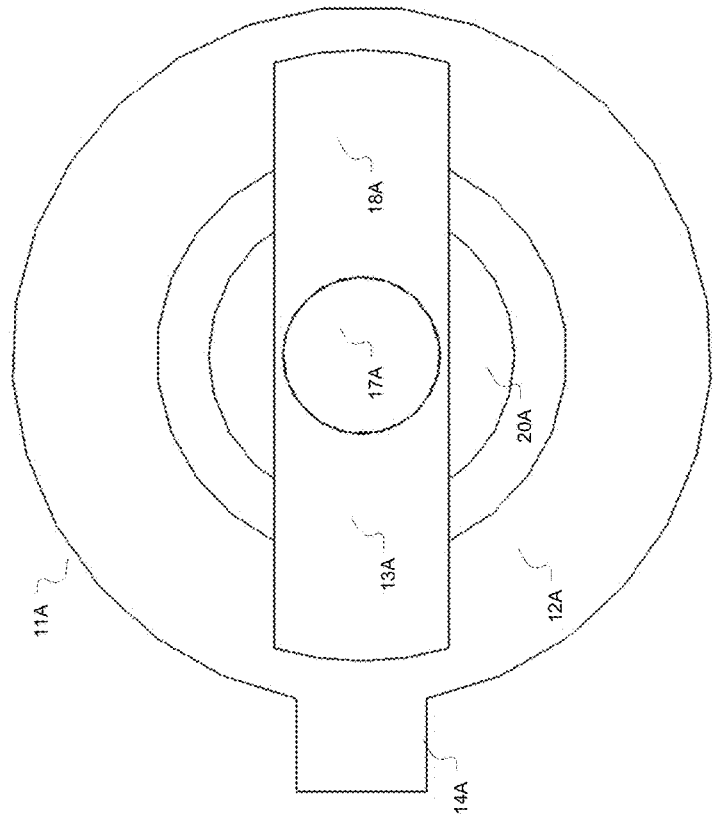
FIG. 2D is a simplified, bottom view of a mammalian tissue region protection system according to various embodiments.
Figure 2C:
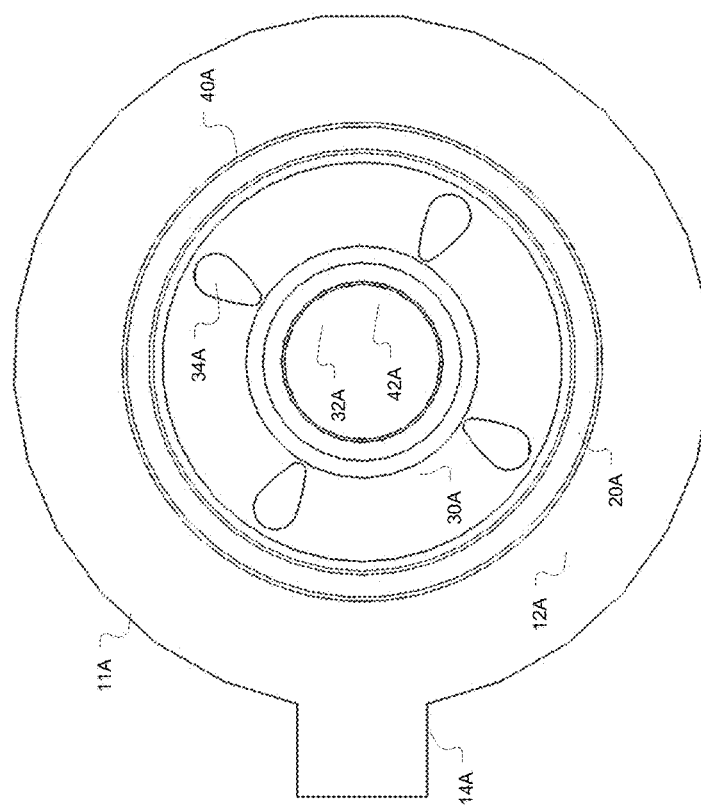
FIG. 2C is a simplified, top view of a mammalian tissue region protection system according to various embodiments.
Figure 9D:
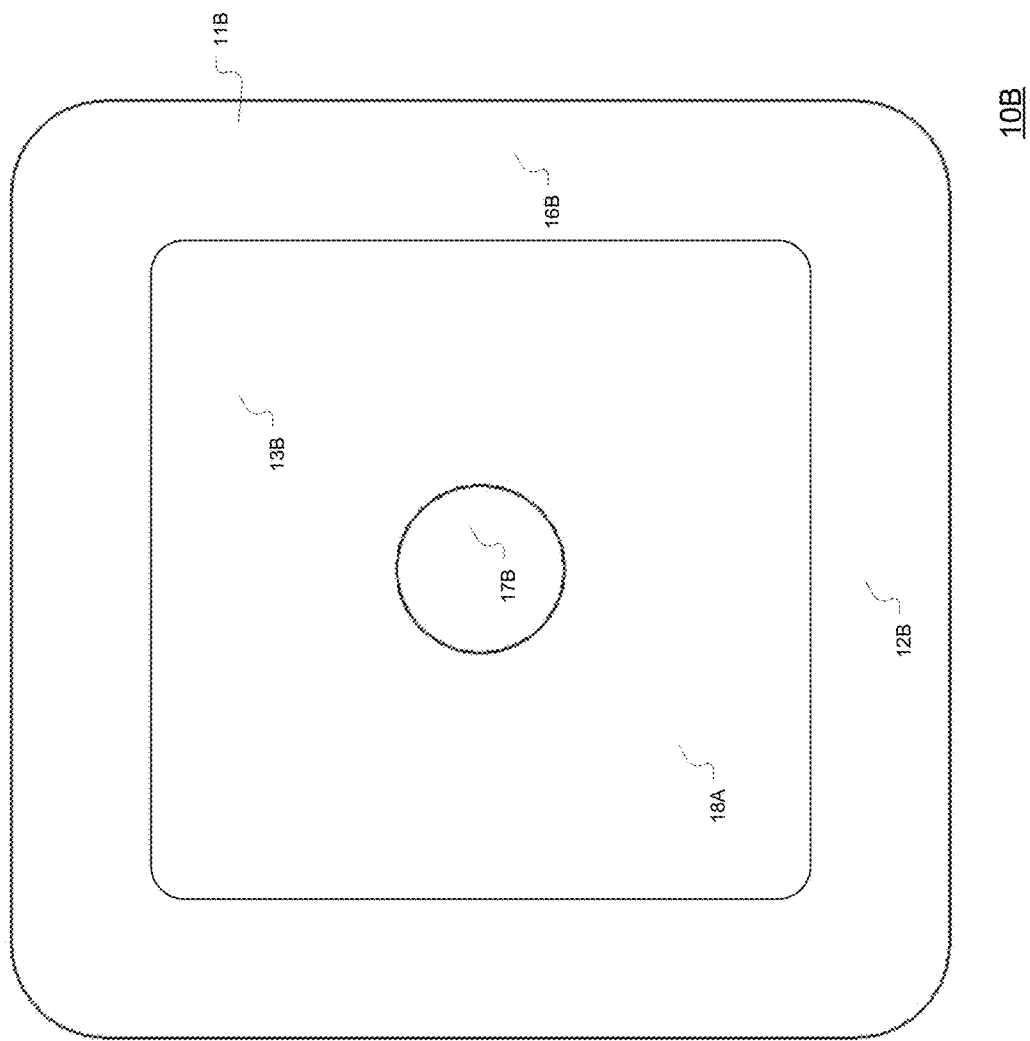
FIG. 9D is a simplified, bottom view of another mammalian tissue region protection system according to various embodiments.

As shown in FIGS. 2B and 9B, a guard module 40A, 40B cap module 30A, 30B may include diametric reduction sections 36A, 36B and 37A, 37B. The one or more diametric reduction sections 36A, 36B and 37A, 37B may reduce the overall bulk, volume, or size of a cap module 30 while providing desired protection of a tissue region 92, 94 and compression rigidity to the guard module 40A, 40B cap module 30A, 30B. FIGS. 2C and 9C are simplified top diagrams of MTRP system 10A, 10B according to various embodiments. As shown in FIGS. 2C, 9C a guard modules 40A, 40B cap module 30A, 30B side fenestrations 34A, 34B may be evenly spaced about its central fenestration 32A, 32B and may be located in the second diametric reduction section 37A, 37B. FIGS. 2D, 9D are simplified bottom view diagrams of MTRP system 10A, 10B according to various embodiments. As shown in FIGS. 2D, 9D, a MTRP system 10A, 10B skin and guard coupling module 11A, 11B may include a non-adhesive section 13A, 13B adjacent an adhesive section. The non-adhesive section 13A, 13B may include a fenestration 17A, 17B that is co-axial with the guard module 40A, 40B fenestration 42A, 42B formed by the base module 20A, 20B fenestration 22A, 22B and the cap module 30A, 30B fenestration 32A, 32B. As noted in an embodiment, the non-adhesive section 13A, 13B may include medically approved absorbent or cushioning material.

Figure 3A:
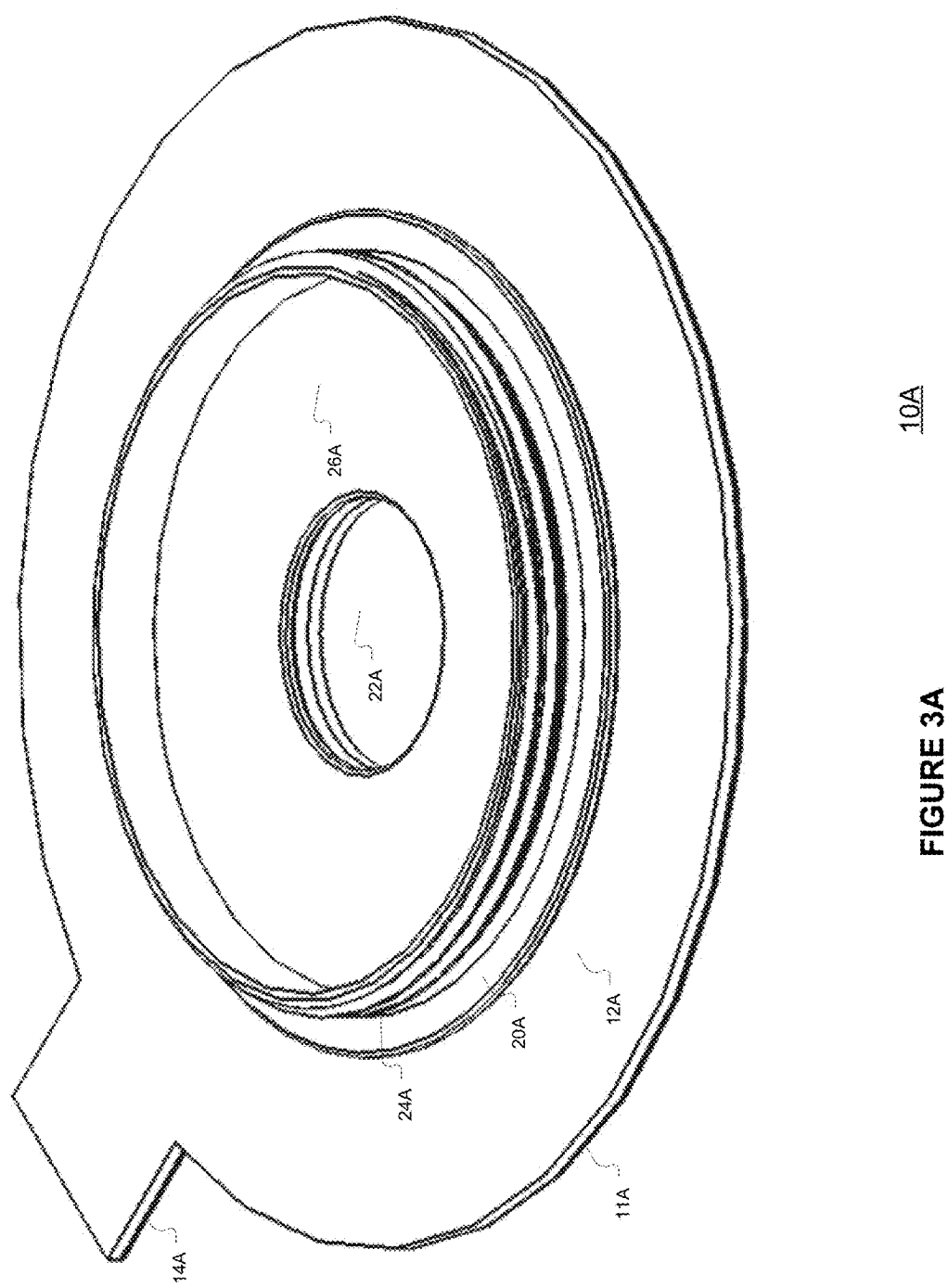
FIG. 3A is a simplified, isometric side view of a mammalian tissue region protection system without the guard cap according to various embodiments.
Figure 10A:
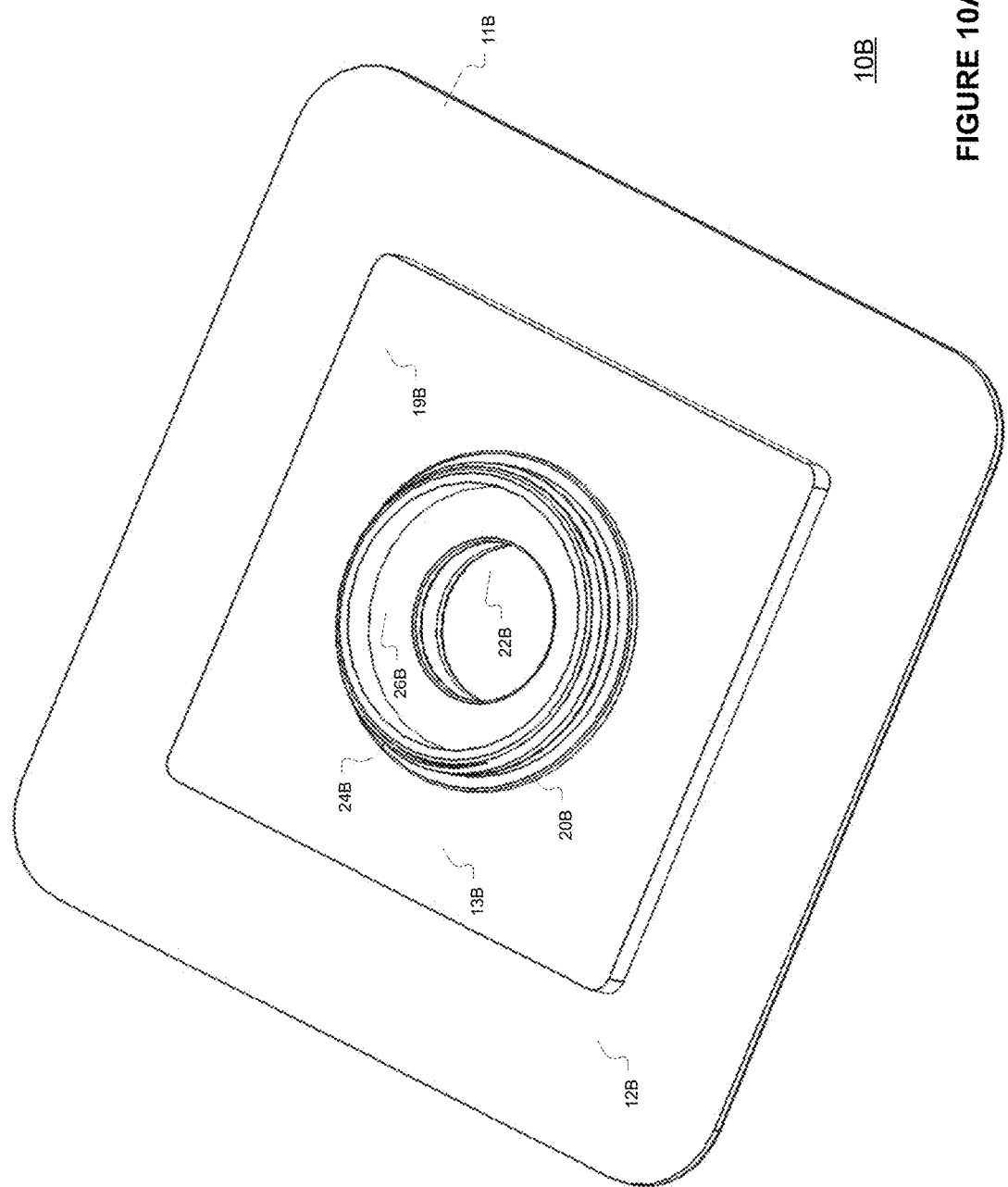
FIG. 10A is a simplified, isometric side view of another mammalian tissue region protection system without the guard cap according to various embodiments.

FIGS. 3A, 10A are simplified isometric diagrams of MTRP systems 10A, 10B with a guard module 40A, 40B cap module 30A, 30B removed according to various embodiments. As shown in FIGS. 3A, 10A, a guard module 40A, 40B base module 20A, 20B may include a coupling mechanism 24A, 24B, a central fenestration 22A, 22B, and a base ring 26A, 26B. The base ring 26A, 26B may extend from the coupling mechanism 24A, 24B to form the central fenestration 22A, 22B. In an embodiment, the base module 20A, 20B fenestration 22A, 22B area may be larger than the corresponding skin and guard coupling module 11A, 11B fenestration 17A, 17B and the mating cap module 30A, 30B fenestration 32A, 32B. In an embodiment, the base ring 26A, 26B extension from the coupling mechanism 24A, 24B may be nominal (about 0.5 to 1 cm) but desirable to increase the surface area contact between the base module 20A, 20B and the skin and guard coupling module 11A, 11B cover 19A, 19B for stable and secure coupling between the modules 20A and 11A and 20B and 11B.

Figure 3B:
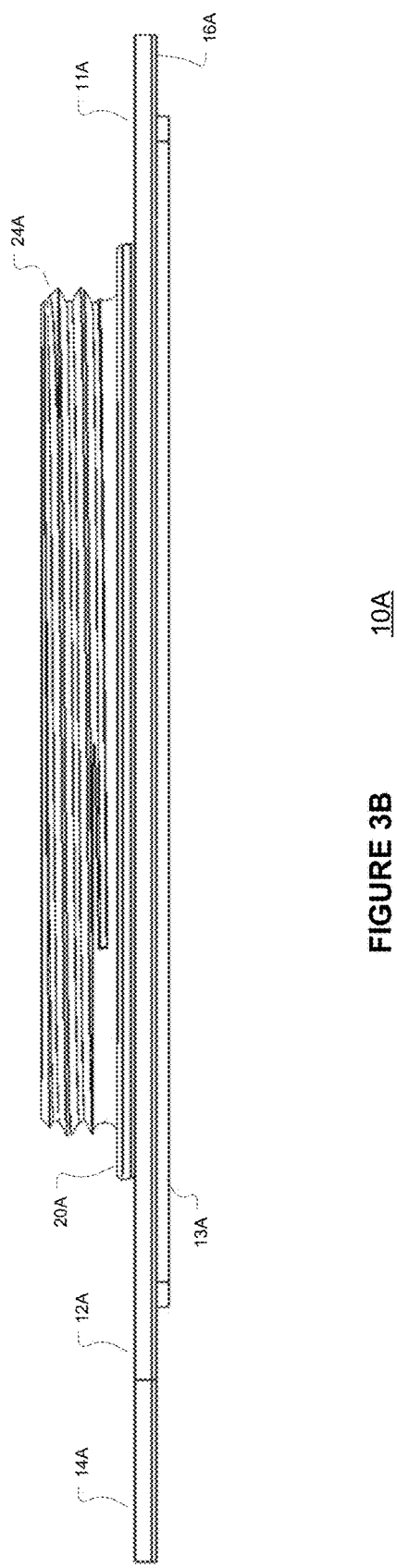
FIG. 3B is a simplified, side view of a mammalian tissue region protection system without the guard cap according to various embodiments.
Figure 10B:
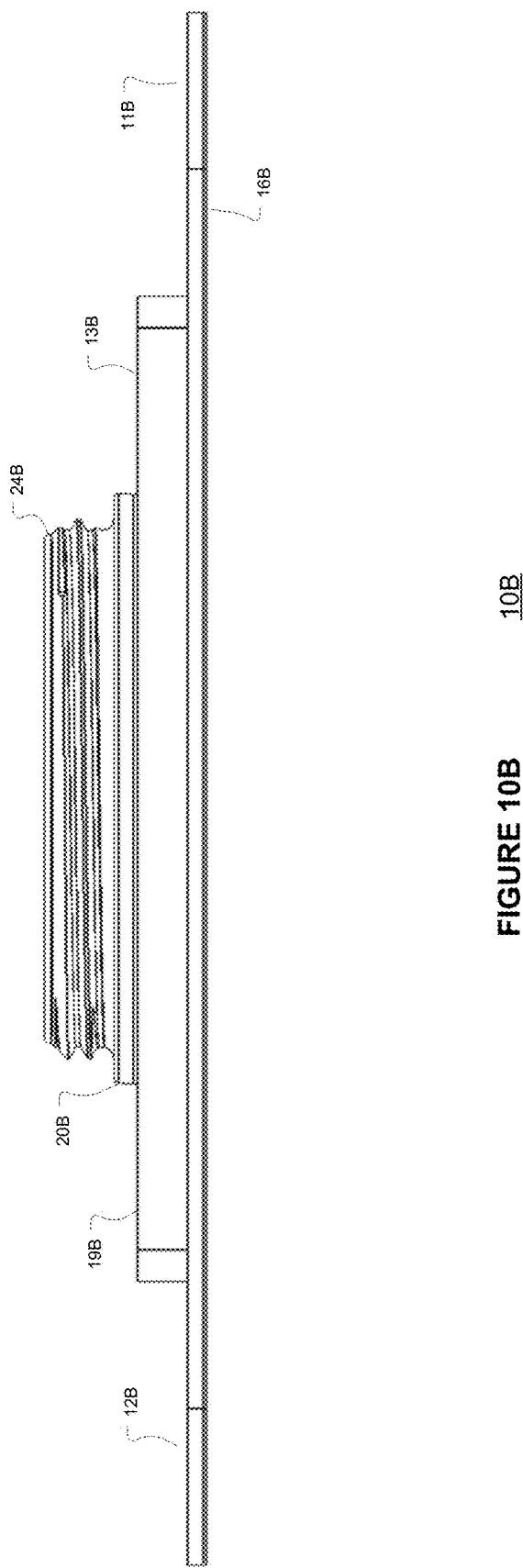
FIG. 10B is a simplified, side view of another mammalian tissue region protection system without the guard cap according to various embodiments.

In an embodiment, a cap module coupling mechanism 24A, 24B may include an external thread 24A, 24B, a snap locking mechanism (66, FIG. 5), or other interlocking mechanism. FIGS. 3B and 10B are simplified side diagrams and FIGS. 3C and 10C are simplified top diagrams of MTRP systems 10A, 10B a guard module 40A, 40B cap module 30A, 30B removed according to various embodiments. As shown in FIG. 3B, a MTRP system 10A skin and guard coupling module 11A non-adhesive layer 13A adjacent the adhesive section 12A may be configured and sized to co-linear with the tab section 14A.

Figure 4A:
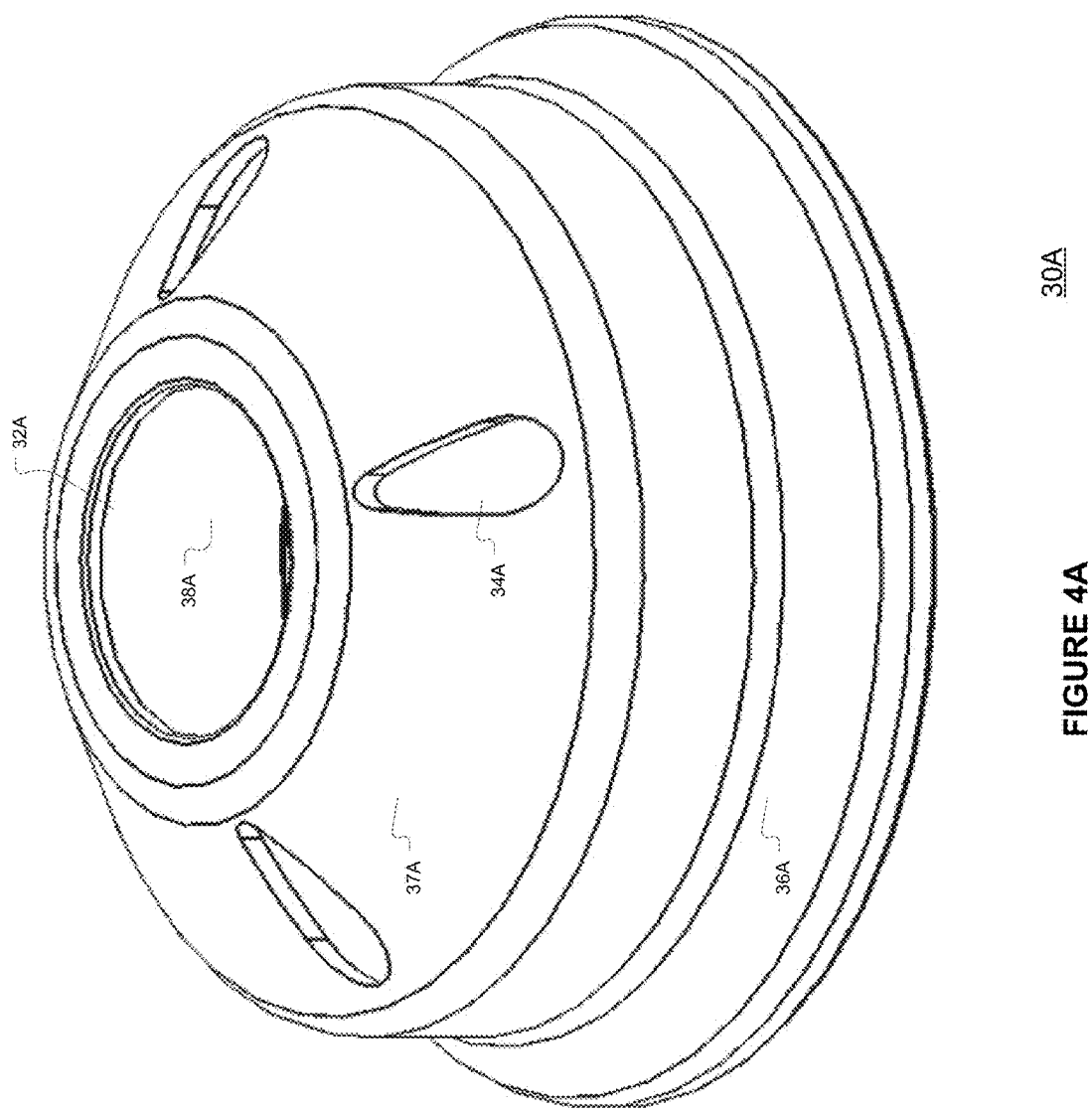
FIG. 4A is a simplified, isometric side view of a mammalian tissue region protection system guard cap according to various embodiments.
Figure 4B:
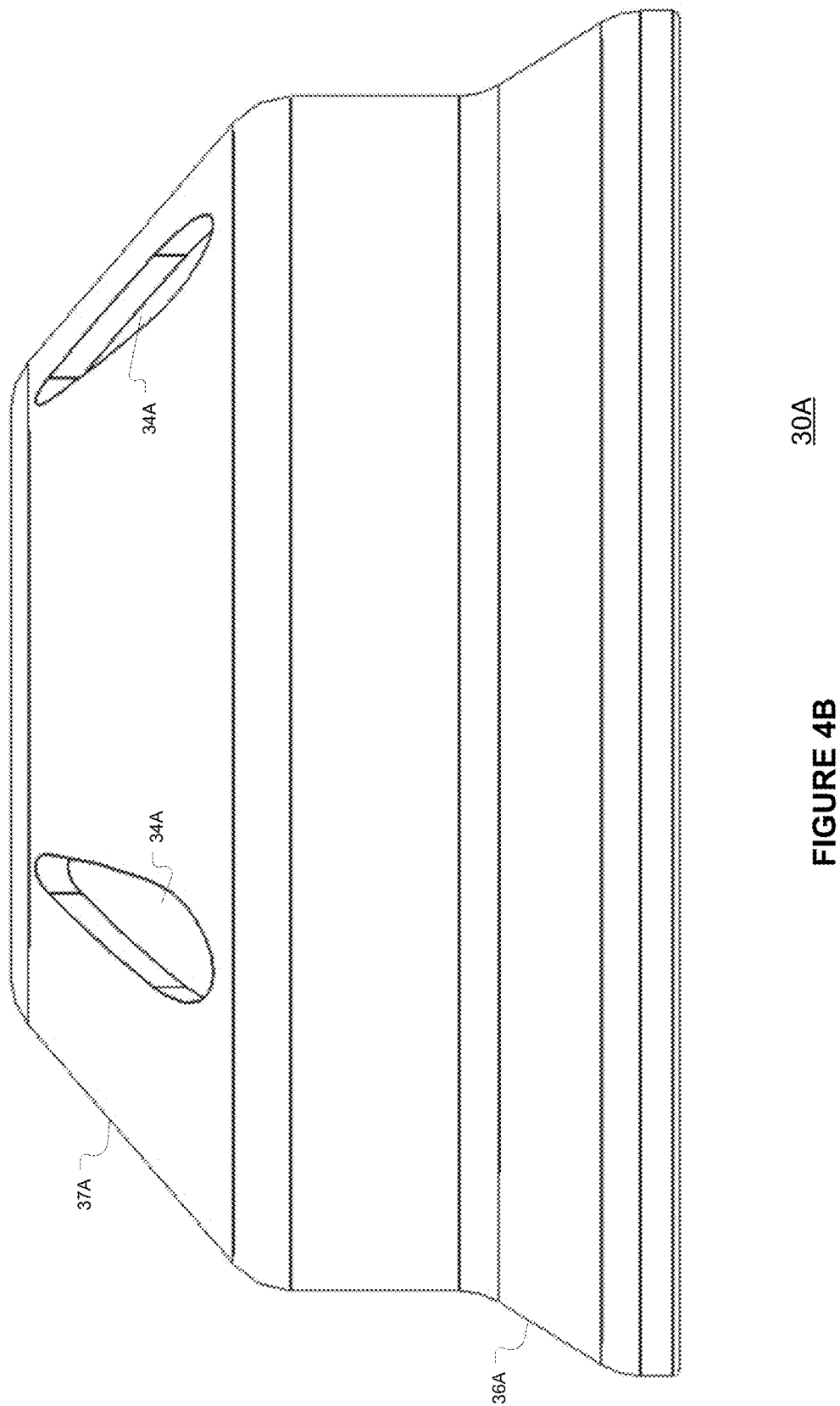
FIG. 4B is a simplified, side view of a mammalian tissue region protection system guard cap according to various embodiments.
Figure 11A:
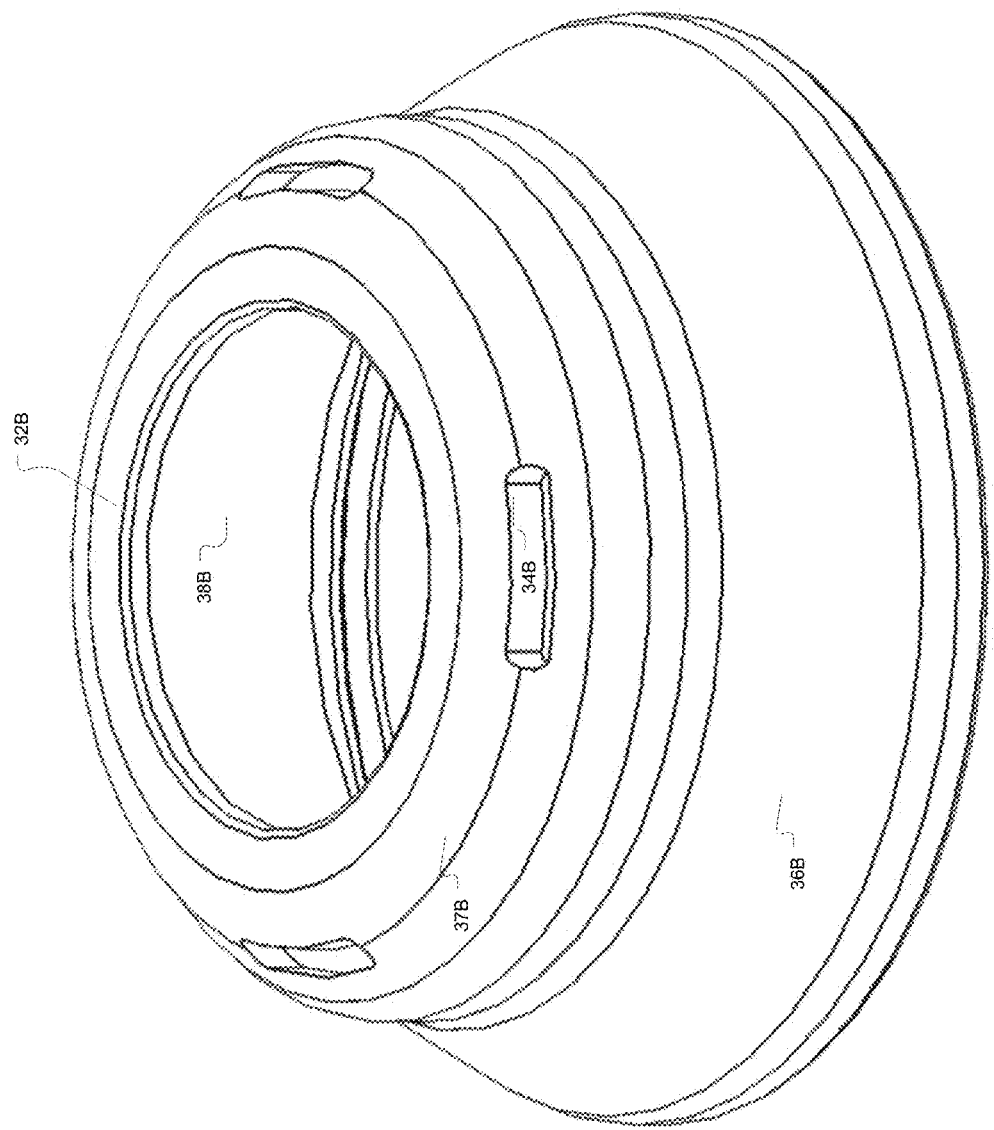
FIG. 11A is a simplified, isometric side view of another mammalian tissue region protection system guard cap according to various embodiments.
Figure 11B:
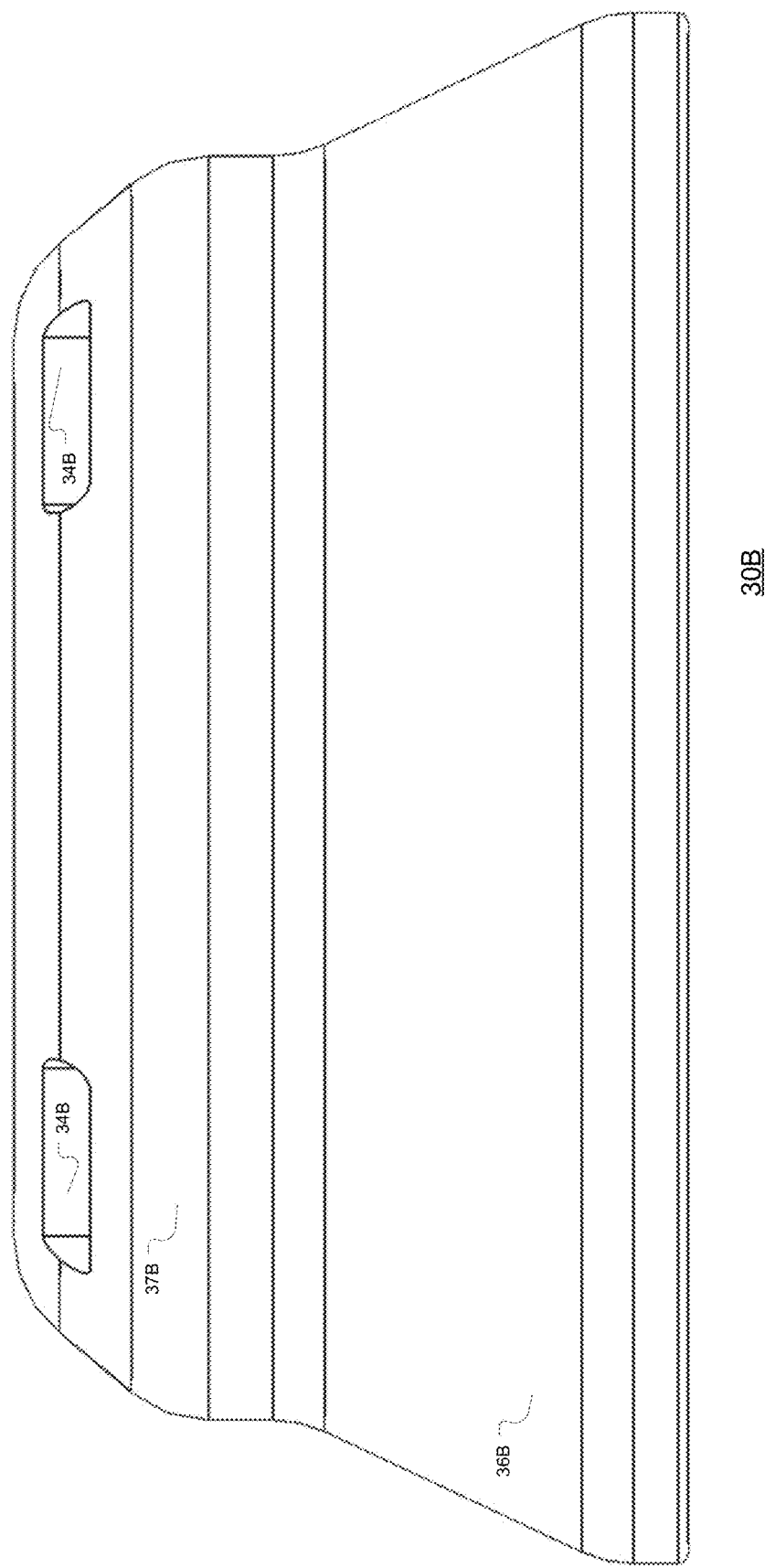
FIG. 11B is a simplified, side view of another mammalian tissue region protection system guard cap according to various embodiments.

FIGS. 4A, 11A are simplified isometric diagrams of MTRP systems 10A, 10B guard module 40A, 40B cap modules 30A, 30B according to various embodiments. FIGS. 4B, 11B are simplified side diagrams and FIGS. 4C, 11C are simplified top diagrams of MTRP systems 10A, 10B guard module 40A, 40B cap modules 30A, 30B according to various embodiments. FIGS. 4D, 11D are simplified bottom diagrams of MTRP systems 10A, 10B guard module 40A, 40B cap modules 30A, 30B according to various embodiments. As shown in FIG. 4A to 4D and 11A to 11D, a guard module 40A, 40B cap 30A, 30B may include a base module 20A, 20B coupling mechanism 31A, 31B. In an embodiment, a cap module 30A, 30B coupling mechanism 31A, 31B may include internal threads or flanges configured to securely and rotatably couple with a guard module 40A, 40B base module 20A, 20B coupling mechanism 24A, 24B corresponding threads or flanges.

Figure 5:
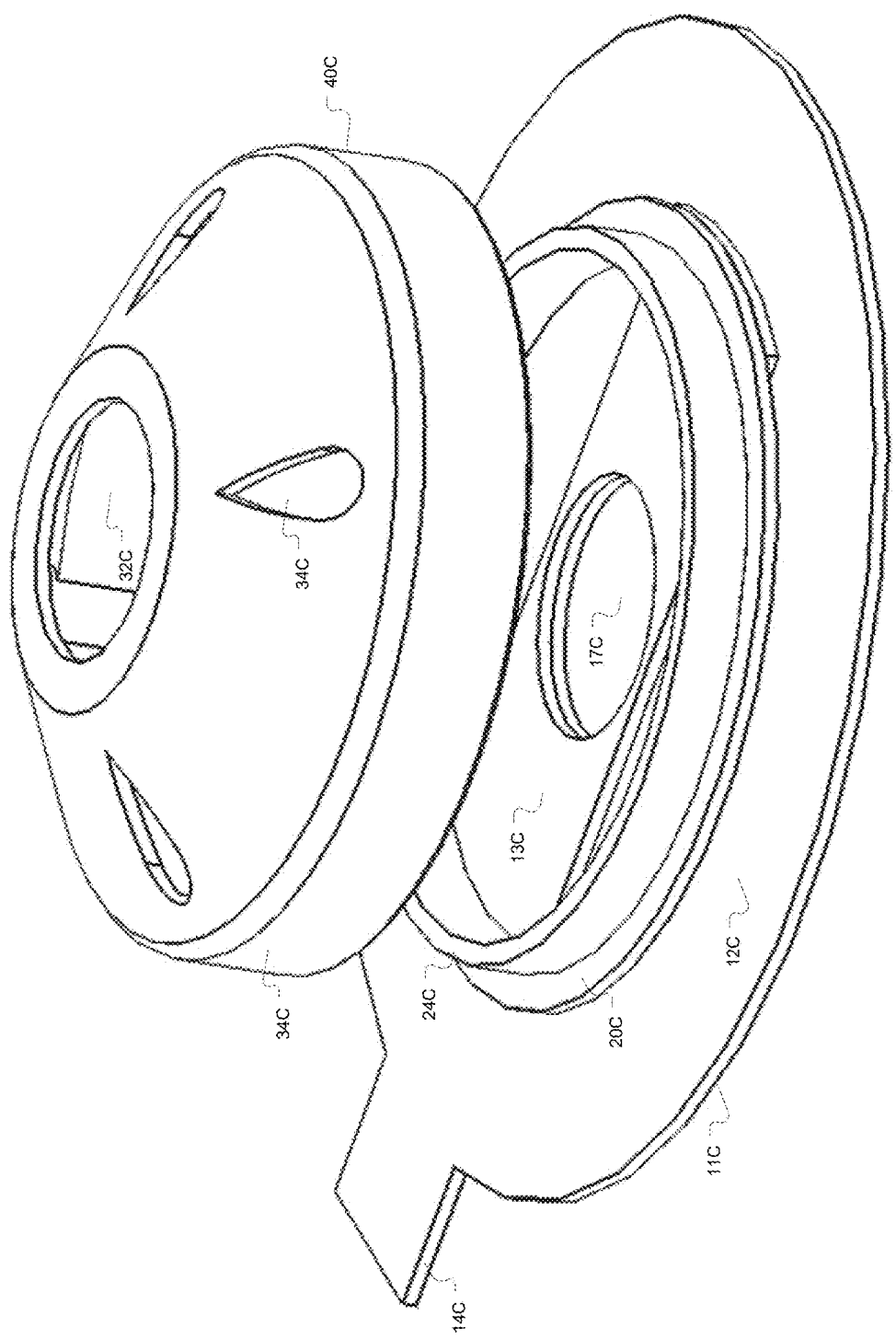
FIG. 5 is a simplified, isometric side view of another mammalian tissue region protection system according to various embodiments.

FIG. 5 is a simplified isometric diagram of a MTRP system 10C according to various embodiments. As shown in FIG. 5, the system 10C may include a skin and guard coupling module 11A and a guard module 40C. The guard module 40C may include a base module 20C and a cap module 30C. In FIG. 5 the cap module 30C is separated from the base module 20C. In an embodiment, a base module 20C may include a snap lock coupling mechanism 24C. The snap lock mechanism 24C may enable a guard module cap module 30C to be securely coupled to the base module 20C. The snap lock mechanism 24C may also enable a cap module 30C to be removed from a base module 20C.

Figure 6:
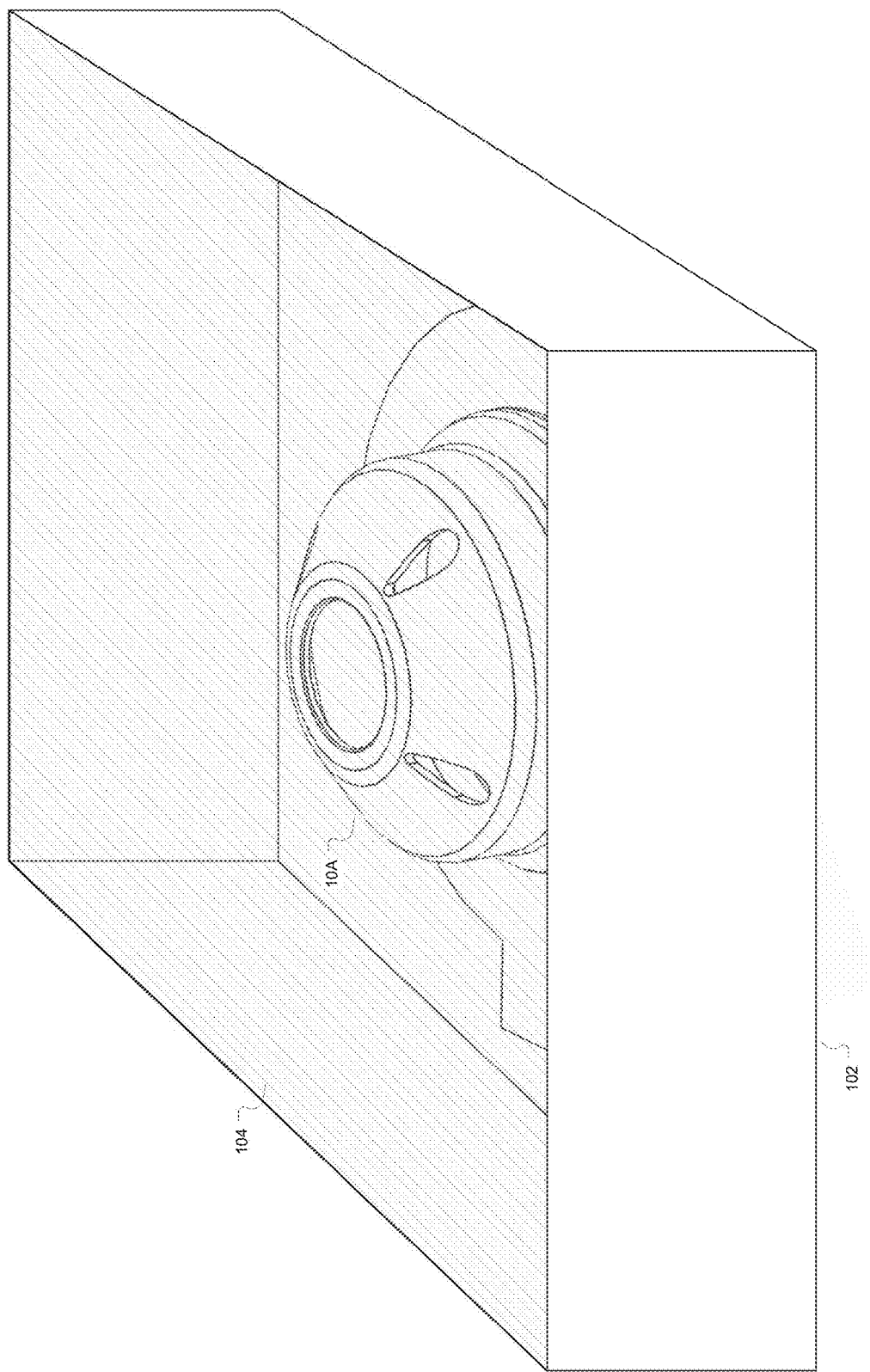
FIG. 6 is a simplified, isometric side view of another mammalian tissue region protection sterile package according to various embodiments.

FIG. 6 is a simplified, isometric side view of another mammalian tissue region protection (MTRP) sterile package 100 according to various embodiments. As shown in FIG. 6, a MTRP sterile or surgical package 100 may include a MTRP system 10A and packaging 102. The packaging 102 may include a clear or opaque layer 104 that hermetically seals a MTRP 10A, 10B, 10C within the packaging 102. In an embodiment, a MTRP system 10A, 10B may be sterile and then sealed within the packaging 102 to create a MTRP sterile package 100. In an embodiment, a MTRP 10A, 10B, 10C system may be provided in non-sterile packaging for non-surgical use.

FIGS. 7A-7B are flow diagrams illustrating mammalian tissue region protection processing algorithms 300, 320 according to various embodiments. In an embodiment, a MTRP system 100 may be employed during a surgical procedure in a sterile environment or field. As noted above, different size and shaped MTRP systems 10A, 10B may be produced for different tissue region deployments or protection. A surgeon or medical professional may select a MTRP system 10A, 10B stored in sterile packaging 102 having a size and shape matching a tissue region to be protected (activity 302). After a MTRP system 10A, 10B having a desired size and shape is selected, it may be removed from its packaging 102 (activity 304). As noted in an embodiment, the packaging 102 may not be sterile for all applications (such as consumer use or doctor's use in office) where a sterile MTRP system 10A, 10B is not required.

A user or medical professional may then remove a skin and guard coupling module 11A, 11B, 11C adhesive section 12A, 12B, 12C cover 16A, 16B from a MTRP system 10A, 10B, 10C to expose adhesive 15A, 15B (activity 306). The MTRP system 10A. 10B may be placed over and coupled to a tissue area 92, 94 to be protected (activity 308) where the MTRP 10A, 10B fenestrations 17A-C and 32A-C are placed over sensitive tissue 94 that is desired to be exposed to air, uncompressed, and protected from compression. In an embodiment, removing the covering 16A, 16B exposes an adhesive section 12A-C and a non-adhesive section 13A-C. In an embodiment, a guard module 40A-C cap 30A-C may be separated from the MTRP system 10A-10C while in the packaging 102 and a clinician, user, or medical professional may couple a guard module 40A-40C cap module 30A-C to a base module 20A-C after placing the cap-less MTRP system 10A-C over an area 92, 94 to be protected (activity 308).

After a MTRP system 10A-C has been placed on a tissue region 92, 94 to be protected (including a guard module 40A-C cap module 30A-C), a clinician, user, or medical professional may employ the process 320 shown in FIG. 7B to inspect a protected area 92, 94. As shown in FIG. 7B, a clinician, user, or medical professional may remove a guard module 40A-C cap module 30A-C from a MTRP system 10A-C that is covering a tissue region 92, 94 (activity 312) to inspect the tissue area 92, 94 covered by the cap module 30A-C (activity 314). A user may apply therapy to an area 94 via the opening 17A-C shown after cap module 30A-30C removal. As a function of the inspection (activity 316), a clinician, user, or medical professional may replace a cap module 30A-C on a corresponding base module 20A-C (securely recouple to base module 20A-C) (activity 318).

A clinician, user, or medical professional may also remove a skin and coupling module 11A-C (an entire MTRP system 10A-C) to expose a larger area 92, 94 (activity 322). When a MTRP system 10A-C is removed, a user may employ the process 300 (activity 324) to place a MTRP system 10A-C over a tissue region 92, 94 to be protected after applying therapy (activity 322) as required. Otherwise, a clinician, user, or medical professional may securely recouple a cap module 30A-C on a corresponding or matable base module 20A-C (activity 318). In an embodiment, a new or different cap module 30A-C may be securely coupled to the base module 20A-C after an existing cap module 30A-C has been removed.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

What is claimed is:

1. A mammalian tissue protection system for protecting a mammalian tissue section, including:

a tissue module, the tissue module including an absorbent layer positioned below a tissue adhering layer, each layer being substantially planar and a co-aligned central fenestration in each layer, extending between the layers, the central fenestration having an opening sized to be greater than the mammalian tissue section to be protected, the tissue adhering layer including a tissue adhesive on its lower side enabling the tissue module to be securely and removably coupled about the mammalian tissue section to be protected; and a guard module, the guard module including a base module and a cap module, the base module including a central fenestration and a base module coupling mechanism, the base module securely coupled above the tissue module tissue adhering layer, at least a portion of the tissue module absorbent layer and tissue adhering layer central fenestrations are co-aligned with base module central fenestration; and the cap module including a substantially incompressible vertical extension between a base and a top, a central fenestration in its top and its base, and a complementary base module coupling mechanism in its base, the cap module securely and removably couplable to the base module and wherein at least a portion of the tissue module's absorbent layer and tissue adhering layer central fenestrations, the base module's central fenestration, and the cap module's central fenestration are co-aligned and provide a substantially incompressible, viewable region.

2. The mammalian tissue protection system of claim 1, wherein the absorbent layer is approximately rectangular in shape and the tissue adhering layer is approximately circular in shape.

3. The mammalian tissue protection system of claim 2, wherein the tissue adhering layer is larger in size than the base module.

4. The mammalian tissue protection system of claim 1, wherein the absorbent layer includes a multiple ply liquid absorbent material.

5. The mammalian tissue protection system of claim 1, wherein the tissue adhering layer's upper side is covered with a substantially liquid impermeable material.

6. The mammalian tissue protection system of claim 1, wherein the complementary base module coupling mechanism includes a thread and the base module coupling mechanism includes a corresponding mating thread.

7. The mammalian tissue protection system of claim 1, wherein the complementary base module coupling mechanism includes an internal thread and the base module coupling mechanism includes a corresponding external mating thread.

8. The mammalian tissue protection system of claim 1, wherein the cap module is formed of a semi-rigid polymer.

9. The mammalian tissue protection system of claim 8, wherein the cap module top includes a plurality of fenestrations that are offset from and non-connecting with its top central fenestration and its base central fenestration.

10. The mammalian tissue protection system of claim 9, wherein each of the plurality of offset fenestrations are smaller in area than the cap module's top central fenestration.

11. The mammalian tissue protection system of claim 1, wherein the tissue module absorbent layer central fenestration, the tissue adhering layer central fenestration, the base module central fenestration, and the cap module base central fenestration are sized to protect one of a nipple or nipple construct.

12. The mammalian tissue protection system of claim 1, wherein the base module and cap module base are each approximately circular in shape.

13. The mammalian tissue protection system of claim 1, wherein the tissue module absorbent layer central fenestration, tissue adhering layer central fenestration, the base module central fenestration, and the cap module base central fenestration have a diameter of about 1 to 3 cm.

\* \* \* \* \*